US012588920B2

(12) United States Patent　(10) Patent No.:　US 12,588,920 B2
Schings et al.　(45) Date of Patent:　Mar. 31, 2026

(54) CLAMPING LOCKOUT FOR LINEAR SURGICAL STAPLER

(71) Applicant: Cilag GmbH International, Zug (CH)

(72) Inventors: Brian D. Schings, Maineville, OH (US); Andrew C. Deck, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 120 days.

(21) Appl. No.: 18/504,247

(22) Filed: Nov. 8, 2023

(65) Prior Publication Data

US 2025/0143735 A1　May 8, 2025

(51) Int. Cl.
　A61B 17/28　　(2006.01)
　A61B 17/072　　(2006.01)
(52) U.S. Cl.
　CPC　*A61B 17/2833* (2013.01); *A61B 2017/07257* (2013.01); *A61B 2017/07271* (2013.01)
(58) Field of Classification Search
　CPC ...... A61B 17/2833; A61B 2017/07257; A61B 2017/07271
　See application file for complete search history.

(56) References Cited

U.S. PATENT DOCUMENTS

| | | | | | |
|---|---|---|---|---|---|
| 4,892,244 | A | * | 1/1990 | Fox | B25C 5/1686 |
| | | | | | 227/176.1 |
| 5,415,335 | A | * | 5/1995 | Knodell, Jr. | A61B 17/07207 |
| | | | | | 227/19 |
| 5,680,983 | A | * | 10/1997 | Plyley | A61B 17/07207 |
| | | | | | 227/175.3 |
| 5,718,359 | A | * | 2/1998 | Palmer | A61B 17/07207 |
| | | | | | 227/176.1 |
| 7,055,730 | B2 | * | 6/2006 | Ehrenfels | A61B 17/07207 |
| | | | | | 227/176.1 |
| 7,419,081 | B2 | * | 9/2008 | Ehrenfels | A61B 17/07207 |
| | | | | | 227/19 |
| 10,631,866 | B2 | | 4/2020 | Laurent et al. | |
| 10,667,818 | B2 | | 6/2020 | McLain et al. | |
| 10,687,819 | B2 | | 6/2020 | Stokes et al. | |
| 10,874,398 | B2 | | 12/2020 | Baxter, III et al. | |

(Continued)

OTHER PUBLICATIONS

International Search Report and Written Opinion dated Mar. 5, 2025, for International Application No. PCT/IB2024/061099, 14 pages.

(Continued)

*Primary Examiner* — Dariush Seif
(74) *Attorney, Agent, or Firm* — FBT Gibbons LLP

(57)　　　　　ABSTRACT

An apparatus includes a housing, a lockout arm, and a spring, and is configured for use with a linear surgical stapler having a first stapler half with a frame and a clamp lever, and a second stapler half with a latch projection. The lockout arm is rotatable between a lockout position and a bypass position and is biased toward the lockout position by the spring. In the lockout position the lockout arm inhibits a proximal end of the clamp lever in a closed state from coupling with a proximal end of the frame. In the bypass position the lockout arm permits the proximal end of the clamp lever in the closed state to couple with the proximal end of the frame. The lockout arm transitions from the lockout position to the bypass position only when the latch projection is properly captured by the clamp lever in the closed state.

20 Claims, 28 Drawing Sheets

(56) References Cited

U.S. PATENT DOCUMENTS

| | | | |
|---|---|---|---|
| 10,898,187 B2 | 1/2021 | Deck et al. | |
| 10,898,197 B2 | 1/2021 | Baxter, III et al. | |
| 10,905,419 B2 | 2/2021 | Schings et al. | |
| 10,932,781 B2 | 3/2021 | Jones et al. | |
| 11,033,266 B2 | 6/2021 | Jones et al. | |
| 11,045,193 B2 | 6/2021 | Schings et al. | |
| 11,219,454 B2 | 1/2022 | Schings et al. | |
| 11,224,425 B2 | 1/2022 | Schings | |
| 11,229,433 B2 | 1/2022 | Schings et al. | |
| 11,278,285 B2 | 3/2022 | Deck et al. | |
| 11,399,827 B2 | 8/2022 | Schings | |
| 11,779,331 B2 * | 10/2023 | Schings | A61B 17/115 227/175.2 |
| 11,937,812 B2 | 3/2024 | Schings et al. | |
| 12,016,555 B2 | 6/2024 | Wang | |
| 12,279,772 B2 * | 4/2025 | Schings | A61B 17/07207 |
| 2004/0007608 A1 * | 1/2004 | Ehrenfels | A61B 17/07207 227/176.1 |
| 2019/0117287 A1 * | 4/2019 | Nativ | A61B 17/07207 |
| 2019/0239881 A1 * | 8/2019 | Laurent | A61B 17/115 |
| 2019/0239882 A1 * | 8/2019 | McLain | A61B 17/1114 |
| 2019/0239883 A1 * | 8/2019 | Baxter, III | A61B 17/115 |
| 2019/0239884 A1 * | 8/2019 | Baxter, III | A61B 17/07207 |
| 2019/0239885 A1 * | 8/2019 | Stokes | A61B 17/115 |
| 2019/0239886 A1 * | 8/2019 | Jones | A61B 17/2833 |
| 2020/0046350 A1 * | 2/2020 | Deck | A61B 17/072 |
| 2020/0046351 A1 * | 2/2020 | Jones | A61B 17/07207 |
| 2020/0046353 A1 * | 2/2020 | Deck | A61B 17/07207 |
| 2020/0113561 A1 * | 4/2020 | Schings | B21K 5/00 |
| 2020/0113562 A1 * | 4/2020 | Schings | A61B 17/1114 |
| 2020/0405298 A1 * | 12/2020 | Ding | A61B 17/0686 |
| 2021/0038223 A1 * | 2/2021 | Schings | A61B 17/0644 |
| 2021/0177408 A1 * | 6/2021 | Schings | A61B 17/07207 |
| 2021/0369270 A1 * | 12/2021 | Schings | A61B 17/07207 |
| 2021/0369271 A1 * | 12/2021 | Schings | A61B 17/072 |
| 2021/0369272 A1 * | 12/2021 | Schings | A61B 17/1114 |
| 2022/0183684 A1 * | 6/2022 | Schings | A61B 17/07207 |
| 2023/0099430 A1 * | 3/2023 | Schings | A61B 17/07207 227/175.2 |
| 2023/0149016 A1 * | 5/2023 | Williams | A61B 17/072 227/175.2 |
| 2023/0397911 A1 | 12/2023 | Deck et al. | |
| 2024/0074749 A1 * | 3/2024 | Schings | A61B 17/07207 |
| 2025/0143735 A1 * | 5/2025 | Schings | A61B 17/2833 |

OTHER PUBLICATIONS

US Design U.S. Appl. No. 29/842,580, filed Jun. 14, 2022, by Schings, et al., entitled: "Staple Cartridge for a Linear Surgical Stapler."

US Design U.S. Appl. No. 29/842,581, filed Jun. 14, 2022, by Deck et al., entitled: "Linear Surgical Stapler."

* cited by examiner

CLAMPING LOCKOUT FOR LINEAR SURGICAL STAPLER

BACKGROUND

In some surgical operations, such as a gastrointestinal anastomosis, it may be desirable to clamp down on one or more layers of tissue, cut through the clamped layers, and simultaneously drive staples through the layers to substantially seal the severed layers together near their severed ends. One such instrument that may be used in such operations is a linear surgical stapler, also referred to as a "linear cutter." A linear surgical stapler generally includes a first half (referred to as a "cartridge half" or "reload half") having a distal jaw configured to support a staple cartridge (or "reload"), and a second half (referred to as an "anvil half") having a distal jaw that supports an anvil surface having staple forming features. The stapler further includes a moveable clamp lever configured to releasably clamp the stapler halves together. The stapler halves are configured to releasably couple together and pivot relative to one another to clamp tissue positioned between the two distal jaws when the clamp lever is closed. A firing assembly of the stapler is configured to be actuated to cut the clamped layers and simultaneously drive staples through the tissue on either side of the cut line. After the stapler is fired, the clamp lever may be opened, and the stapler halves separated to release the severed and stapled tissue.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
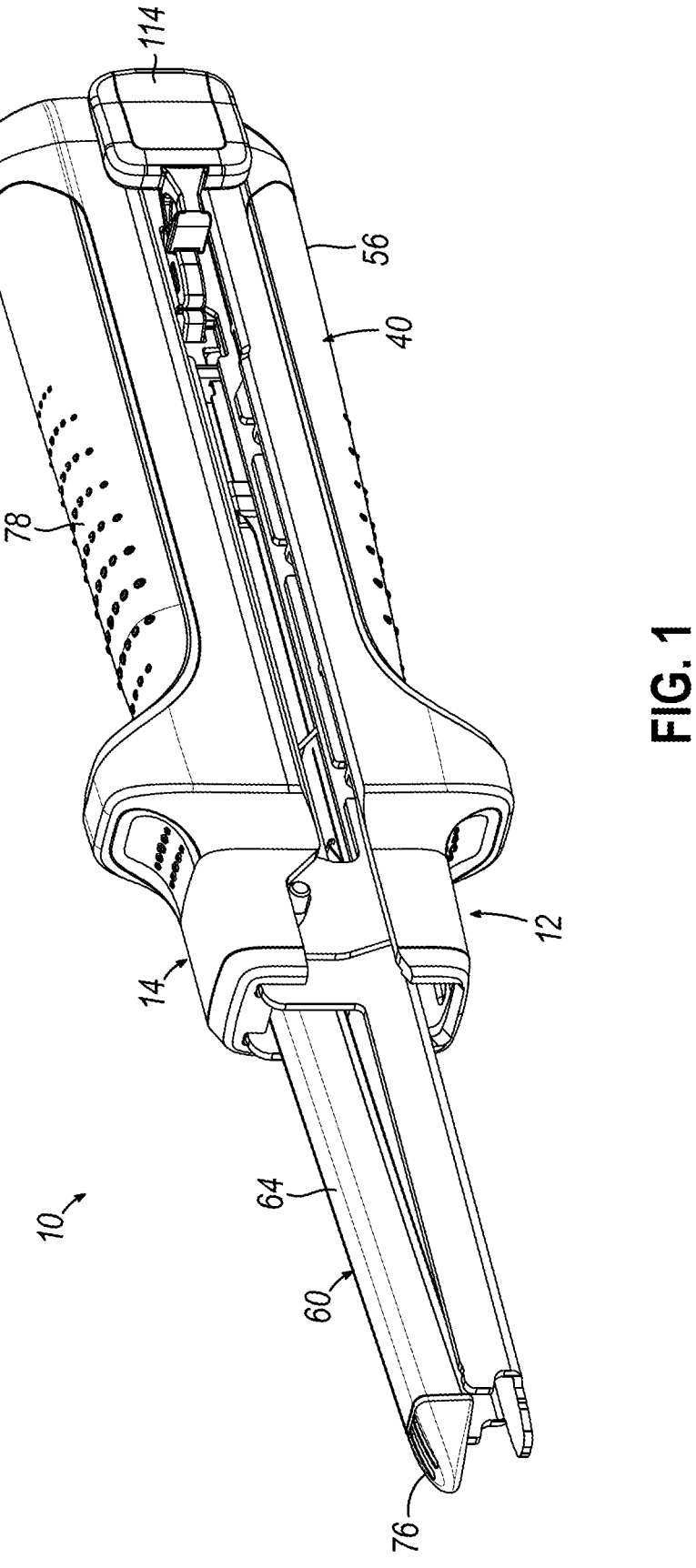
FIG. 1 depicts a perspective view of an illustrative linear surgical stapler, showing a cartridge half and an anvil half of the stapler coupled together with a clamp lever of the cartridge half in a fully closed position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for illustrative description purposes only and are not intended to be limiting or absolute. In that regard, it will be understood that surgical instruments such as those disclosed herein may be used in a variety of orientations and positions not limited to those shown and described herein.

Furthermore, the terms "about" and "approximately" as used herein in connection with any numerical values or ranges indicate a suitable dimensional tolerance that allows the referenced feature(s) to function for its intended purpose as described herein.

I. ILLUSTRATIVE LINEAR SURGICAL STAPLERS

A. Overview of Linear Surgical Stapler

Figure 2:
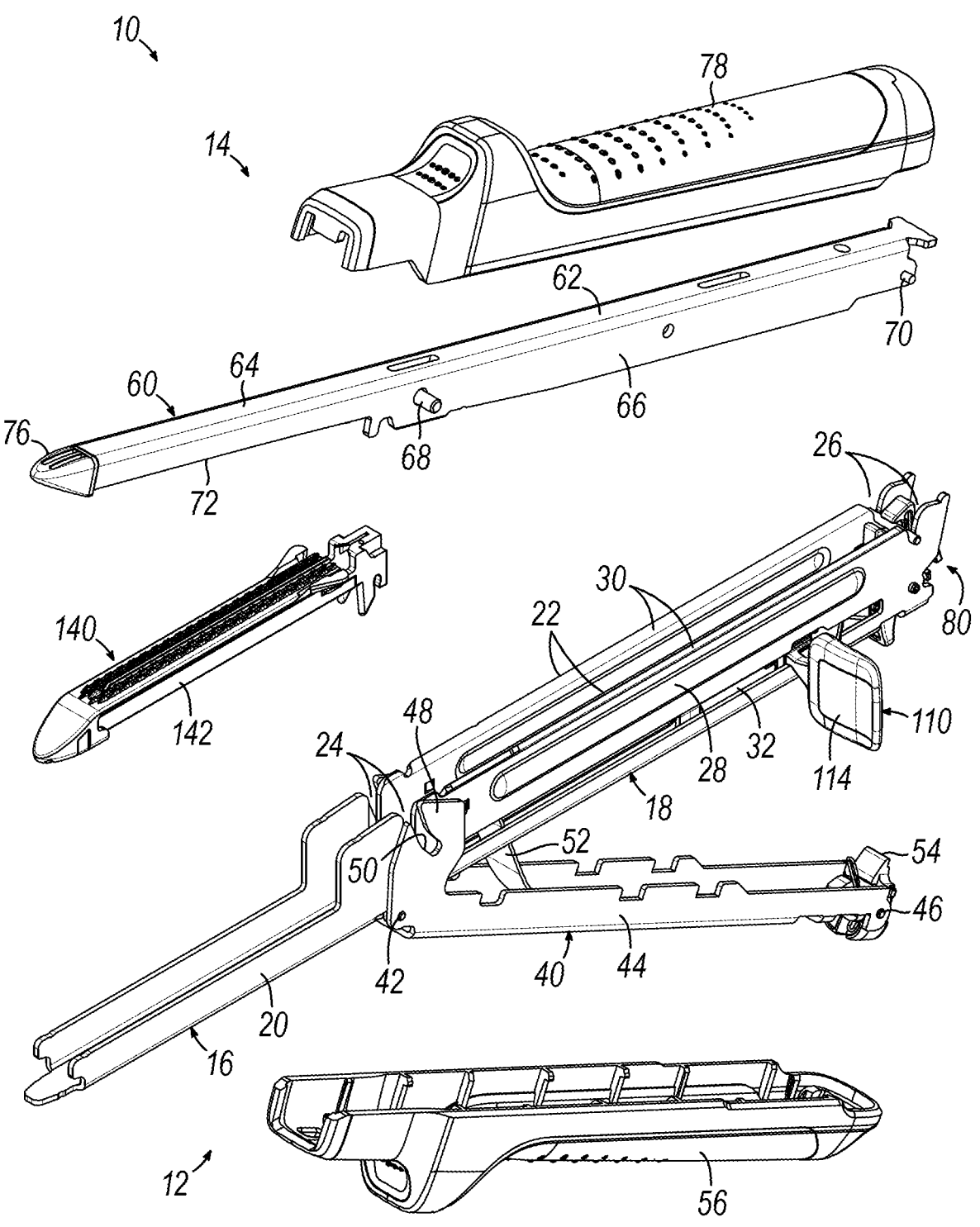
FIG. 2 depicts an exploded perspective view of the linear surgical stapler of FIG. 1, additionally showing a staple cartridge.

FIGS. 1-2 show an illustrative linear surgical stapler (10) (also referred to as a "linear cutter") suitable for use in a variety of cutting and stapling procedures, such as a gastrointestinal anastomosis procedure. Linear surgical stapler (10) includes a cartridge half (12) (also referred to as a "reload half") and an anvil half (14) configured to releasably couple together to clamp tissue therebetween for simultaneous cutting and stapling of the clamped tissue. Linear surgical stapler (10) may be further configured in accordance with the teachings of U.S. patent application Ser. No. 18/316,635, entitled "Linear Surgical Stapler," filed on May 12, 2023, issued as U.S. Pat. No. 12,533,136 on Jan. 27, 2026, the disclosure of which is incorporated by reference herein.

Cartridge half (12) includes a first elongate member in the form of an elongate cartridge channel (16) having a proximal frame portion (18) and a distal jaw portion (20). Proximal frame portion (18) slidably retains a firing assembly (110) and includes a laterally opposed pair of upright side flanges (22). Each side flange (22) includes a vertical slot (24) arranged at a distal end thereof, and a tapered notch (26) arranged at a proximal end thereof. An outwardly projecting stiffening rib (28) extends longitudinally between the distal slot (24) and proximal notch (26) of each side flange (22) and is configured to provide the side flange (22) with enhanced stiffness. An outwardly flared upper segment (30) defines an upper edge of a proximal portion of each side flange (22) and is configured to facilitate receipt of anvil half (14) by cartridge half (12). Each side flange (22) further includes an elongate firing slot (32) extending longitudinally between proximal notch (26) and distal slot (24) along a lower side of side flange (22). Elongate firing slots (32) are configured to guide firing assembly (110) between proximal and distal positions. Firing assembly (110) is described in greater detail below in connection with FIG. 8.

Figure 4:
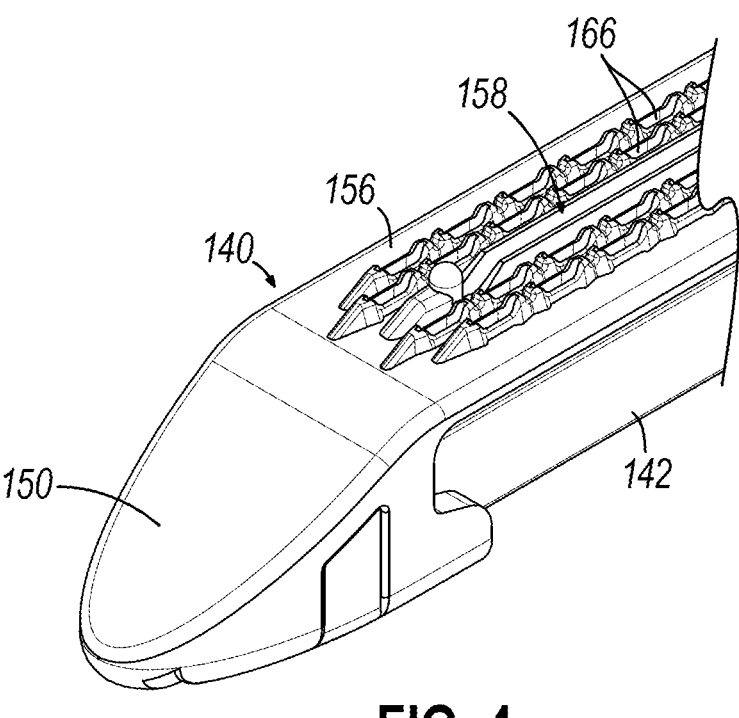
FIG. 4 depicts a perspective view of a distal end portion of the staple cartridge of FIG. 2.

Distal jaw portion (20) of cartridge channel (16) is configured to releasably receive a staple cartridge (140) (or "reload"). As shown in FIG. 4, staple cartridge (140) includes a cartridge body (142) having an upper side that defines a first stapling surface in the form of a deck (156) having a plurality of staple openings (166) that house a plurality of staples (not shown) and corresponding staple drivers (not shown).

Cartridge half (12) further includes a clamp member in the form of a clamp lever (40) (also referred to as a "clamp arm" or "latch lever") pivotably coupled to cartridge channel (16) with a clamp lever pivot pin (42), which is arranged in approximate alignment with distal slots (24) of cartridge channel side flanges (22). Clamp lever (40) includes an elongate lever arm (44) having a free proximal end (46) and a distal end that is pivotably coupled to a lower portion of cartridge channel (16) with pivot pin (42). A pair of opposed jaws (48) extend distally from the distal end of lever arm (44) alongside cartridge channel side flanges (22). Each jaw (48) includes a curved slot (50) having a closed proximal end and an open distal end configured to receive a latch pin (68) of anvil half (14), as described below.

Figure 9A:
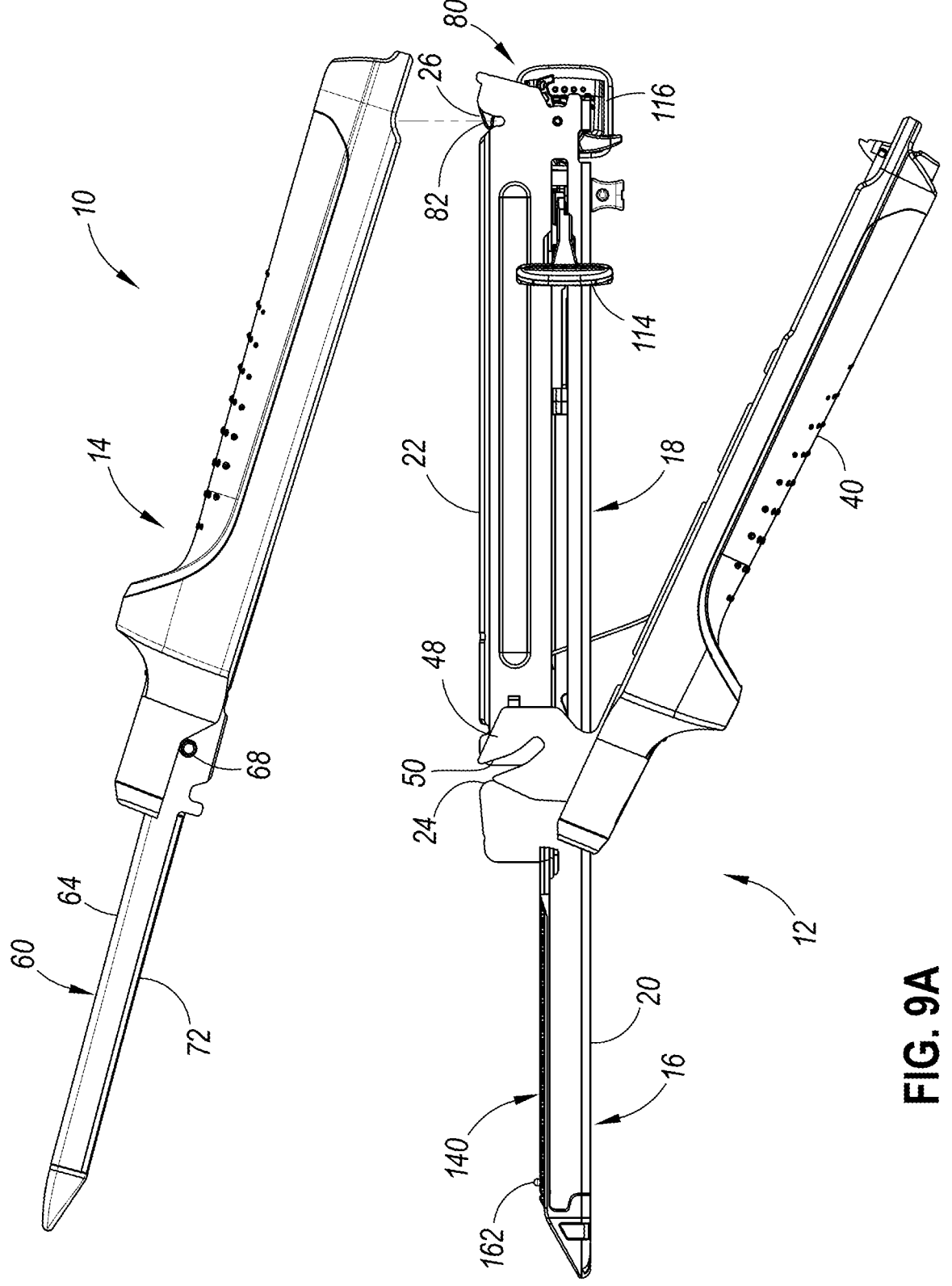
FIG. 9A depicts a side elevational view of the linear surgical stapler of FIG. 1, showing the stapler halves separated from one another with the clamp lever in the open position.
Figure 9B:
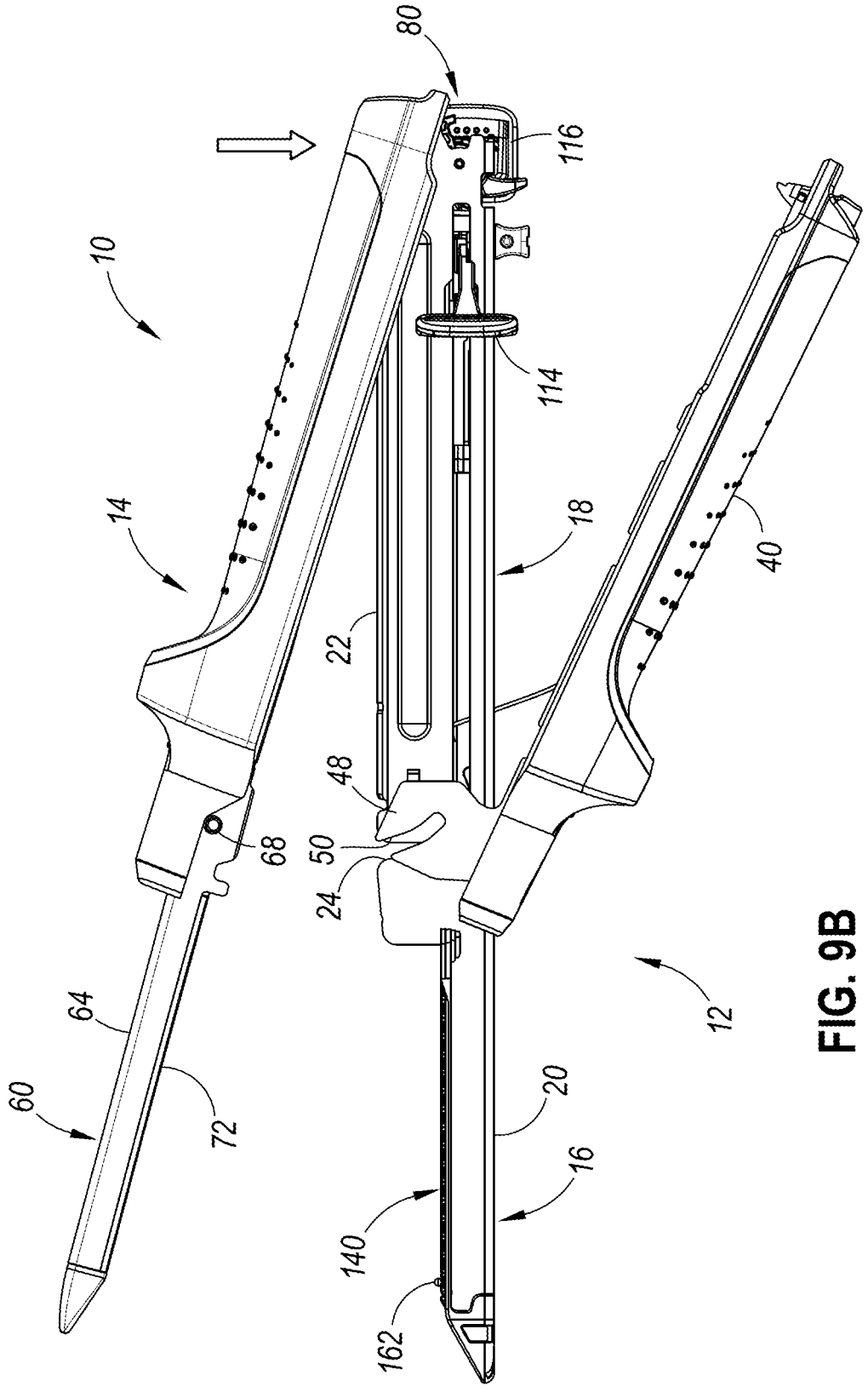
FIG. 9B depicts a side elevational view of the linear surgical stapler of FIG. 1, showing proximal ends of the stapler halves coupled together while the clamp lever is in the open position to provide the stapler in a "hang-open" state.
Figure 9C:
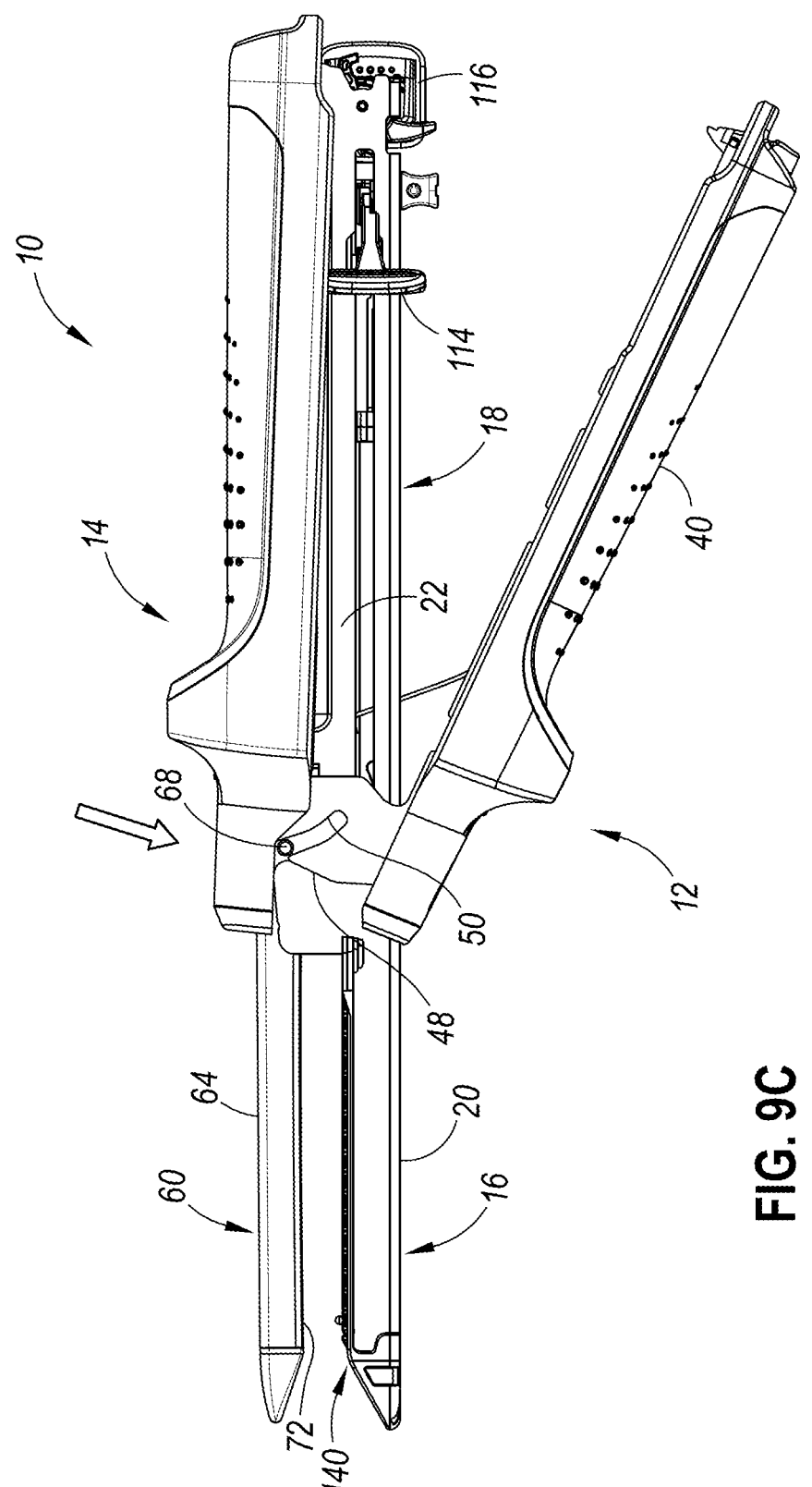
FIG. 9C depicts a side elevational view of the linear surgical stapler of FIG. 1, showing distal portions of the stapler halves having been approximated so that a distal pin of the anvil half is received by clamp lever jaws of the cartridge half.
Figure 9D:
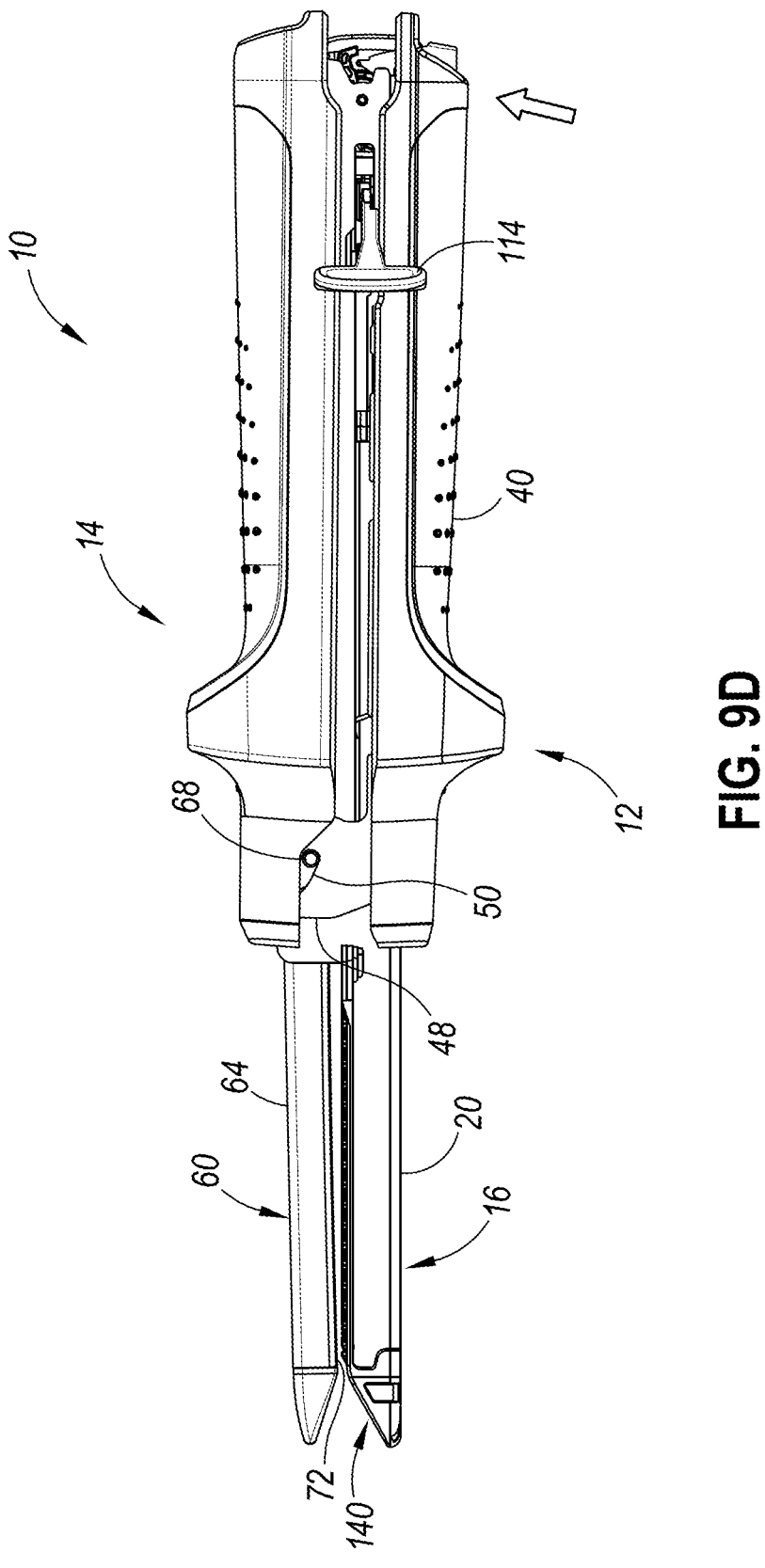
FIG. 9D depicts a side elevational view of the linear surgical stapler of FIG. 1, showing closure of the clamp lever to fully clamp the stapler halves together.

Clamp lever (40) is operable to pivot relative to cartridge channel (16) between an open position in which proximal end (46) of lever arm (44) is spaced from cartridge channel frame portion (18) as shown in FIGS. 9A-9C described below, and a closed position in which proximal end (46) confronts cartridge channel frame portion (18) as shown in FIG. 9D described below. Actuation of clamp lever (40) from the open position to the closed position operates to capture the opposed lateral ends of latch pin (68) within clamp lever jaw slots (50), and thereby clamp anvil half (14) against cartridge half (12), as shown and described below in connection with FIGS. 9C-9D. In that regard, the curvature of each jaw slot (50) defines respective upper and lower camming surfaces configured to engage and draw the respective lateral end of latch pin (68) toward cartridge channel (16) as clamp lever (40) is pivotably closed. A resilient member shown in the form of a leaf spring (52) biases lever arm (44) toward the open position. Accordingly, leaf spring (52) promotes disengagement of clamp lever jaws (48) from anvil half latch pin (68) upon initial advancement of clamp lever (40) from the closed position toward the open position.

As best shown in FIG. 2, clamp lever (40) further includes a latch member (54) arranged at proximal end (46) of lever arm (44). Clamp lever latch member (54) is configured to resiliently and releasably engage a proximal end of cartridge channel frame portion (18) and thereby releasably retain clamp lever (40) in the closed position, for instance while stapler (10) is being fired. Clamp lever latch member (54) may be further configured in accordance with the teachings of U.S. Pat. No. 11,278,285, entitled "Clamping Assembly for Linear Surgical Stapler," issued Mar. 22, 2022, the disclosure of which is incorporated by reference herein.

Anvil half (14) of linear surgical stapler (10) includes a second elongate member in the form of an elongate anvil channel (60) having a proximal frame portion (62) and a distal jaw portion (64). Proximal frame portion (62) includes a laterally opposed pair of upright side flanges (66) that are configured to be received between cartridge channel side flanges (22) when anvil half (14) is coupled with cartridge half (12). A distal latch projection in the form of latch pin (68) extends laterally through the distal ends of anvil channel side flanges (66), and a proximal pivot projection in the form of a proximal pin (70) extends laterally through the proximal ends of anvil channel side flanges (66). Anvil half pins (68, 70) are configured to facilitate coupling of anvil half (14) with cartridge half (12), as described below.

Figure 3:
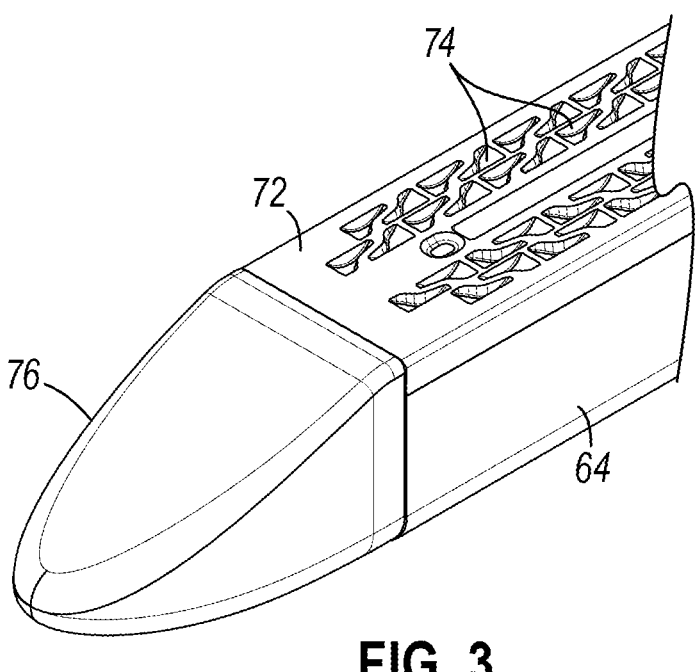
FIG. 3 depicts a perspective view of a distal end portion of the anvil half of the linear surgical stapler of FIG. 1.

As shown in FIGS. 2 and 3, distal jaw portion (64) of anvil half (14) supports an anvil plate (72) that defines a second stapling surface in the form of an anvil surface having a plurality of staple forming pockets (74) configured to deform legs of staples ejected by staple cartridge (140) when stapler (10) is fired. Staple forming pockets (74) of the present example may be formed via a coining process and are configured to form each staple of staple cartridge (140) with a three-dimensional shape in which the legs of each formed staple are laterally offset from one another so as to provide the formed staple with a non-planar shape, for example as disclosed in U.S. Pat. No. 11,229,433, entitled "Linear Surgical Stapler," issued Jan. 25, 2022, the disclosure of which is incorporated by reference herein. Anvil channel (60), anvil plate (72), and staple forming pockets (74) may be formed in one or more of the manners disclosed in U.S. Pat. Nos. 11,229,433; 11,045,193, entitled "Anvil Assembly for Linear Surgical Stapler," issued Jun. 29, 2021; and/or U.S. Pub. No. 2022/0142641, entitled "System and Method for Forming Pockets in Anvil of Surgical Stapler," published May 12, 2022, issued as U.S. Pat. No. 12,016,555 on Jun. 25, 2024, the disclosures of which are incorporated by reference herein. For instance, distal jaw portion (64) of anvil half (14) may be pre-formed with a curvature along its length that accommodates deflection of distal jaw portion (64) and anvil plate (72) when stapler halves (12, 14) are clamped together by clamp lever (40). Distal jaw portion (64) of anvil half (14) additionally supports a tapered distal tip member (76). In some versions, distal tip member (76) may be selectively extendable relative to distal jaw portion (64) in accordance with the teachings of U.S. Pat. No. 11,033,266, entitled "Decoupling Mechanism for Linear Surgical Stapler, issued Jun. 15, 2021, the disclosure of which is incorporated by reference herein.

As shown in FIG. 2, linear surgical stapler (10) further includes a pair of shrouds (56, 78) that cover select portions of stapler (10) and promote effective grip and manipulation of stapler (10) by an operator during use. In the present example, a clamp lever shroud (56) is affixed to and covers an outwardly facing side of clamp lever (40) such that clamp lever shroud (56) is configured to pivot with clamp lever (40) relative to cartridge channel (16). Additionally, an anvil shroud (78) is affixed to and covers an outwardly facing side of anvil channel (60). In some versions, anvil shroud (78) may be coupled with anvil channel (60) via interaction between pins (68, 70) and one or more tabs, ribs, or other structures that are disposed within an interior of anvil shroud (78) and include an opening, slot, keyhole, or other feature configured to receive a respective one of pins (68, 70). By way of example only, shrouds (56, 78) may be affixed using one or more of the teachings of U.S. Pat. No. 11,278,285, incorporated by reference above. In other versions, shrouds (56, 78) may be coupled with clamp lever (40) and anvil channel (60) in a variety of other suitable manners readily apparent to those of ordinary skill in the art in view of the teachings herein.

As shown best in FIGS. 2 and 5-7, a proximal end of cartridge half (12) includes a retaining assembly (80) configured to releasably retain portions of anvil half (14) and firing assembly (110). Retaining assembly (80) of the present example includes a first movable retaining member in the form of an anvil latch member (82) and a second movable retaining member in the form of a detent member (84). Anvil latch member (82) and detent member (84) are rotatably coupled with a proximal end of cartridge channel (16) via a laterally extending pin (85) arranged proximally of firing slots (32), and members (82, 84) are resiliently biased in opposite rotational directions by a resilient member in the form of a torsion spring (86) positioned between members (82, 84).

Anvil latch member (82) includes a central body (88), a latch finger (90) extending upwardly from central body (88), and a release button (92) extending downwardly from central body (88) though a base wall of proximal frame portion (18) of cartridge channel (16). An upper end of latch finger (90) tapers distally and is configured to releasably capture proximal anvil pin (70) of anvil half (14) with an angled latching surface (94) that overlies proximal anvil pin (70) once captured. Anvil latch member (82) further includes a pin ejection feature in the form of an angled projection (96) extending distally from a base portion of latch finger (90) and which defines an ejection cam ramp (98) that faces proximally toward latch finger (90).

Detent member (84) of proximal retaining assembly (80) includes a generally cylindrical central body (100), a distal finger (102) extending distally from central body (100), and a proximal hook (104) extending proximally from central body (100). Distal finger (102) is configured to releasably engage a proximal end of firing assembly (110) and thereby retain firing assembly (110) in a proximal home position. Proximal hook (104) is configured to overlie and capture an upper tip of clamp lever latch member (54) when clamp lever (40) is fully closed and firing assembly (110) is translated distally from its proximal home position, thereby preventing clamp lever (40) from opening during a firing stroke, for example as described in greater detail in U.S. Pat. No. 11,278,285, incorporated by reference above.

In use, with stapler halves (12, 14) coupled together at their proximal ends such that proximal anvil pin (70) is retained by anvil latch member (82), and with clamp lever (40) in the open position, distal actuation of lower release button (92) causes anvil latch member (82) to rotate about pin (85) such that ejection cam ramp (98) advances proximally to drive proximal anvil pin (70) upwardly out of proximal tapered notches (26) of cartridge channel (16). Cartridge half (12) of the present version further includes a stationary finger grip projection (106) that extends downwardly from a base wall of proximal frame portion (18) of cartridge channel (16) at a location distal to lower release button (92) and is configured to facilitate actuation of release button (92). In particular, a user may apply his or her thumb to a proximal side of release button (92) and one or more fingers to a distal side of finger grip projection (106), and then squeeze release button (92) distally toward stationary finger grip projection (106) to rotate latch finger (90) out of engagement with proximal anvil pin (70) and eject pin (70) upwardly from cartridge channel (16) with ejection cam ramp (98).

Retaining assembly (80) and related components of cartridge half (12) may be further configured and operable in accordance with one or more teachings of U.S. Pat. No. 10,898,187, entitled "Firing System for Linear Surgical Stapler," issued Jan. 26, 2021, the disclosure of which is incorporated by reference herein; and/or U.S. Pat. No. 11,033,266, incorporated by reference above.

Figure 8:
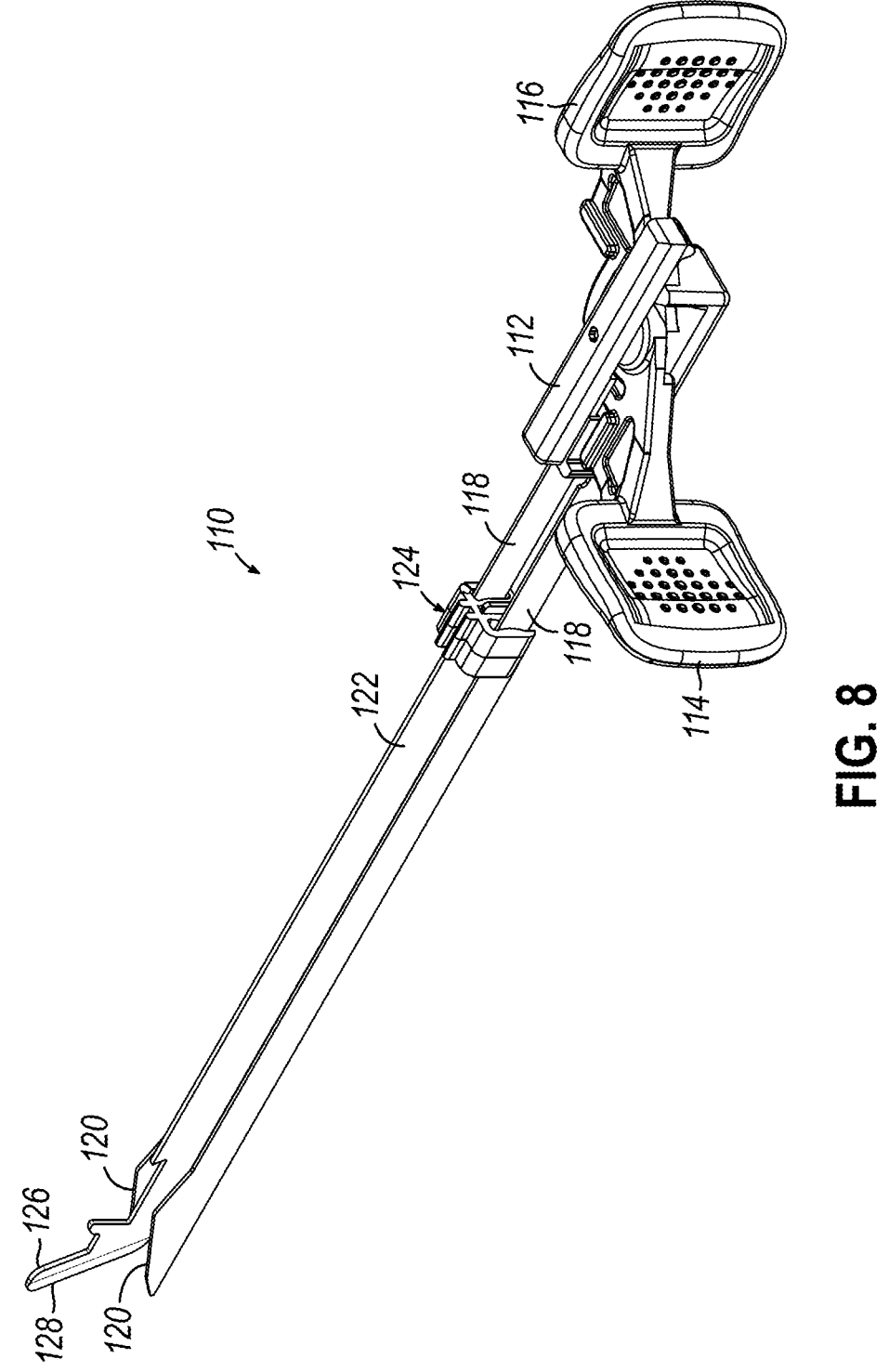
FIG. 8 depicts a perspective view of the firing assembly of FIG. 5.

As shown in FIG. 8, firing assembly (110) of cartridge half (12) includes a slide block (112), a pair of actuators (114, 116) (or "firing knobs") pivotably coupled to slide block (112), and a set of elongate beams (118, 122) extending distally from slide block (112). A pair of side beams (118) are coupled at their proximal ends to a distal end of slide block (112) and terminate distally in a pair of cam ramps (120). Cam ramps (120) are configured to engage the undersides of staple drivers (not shown) housed within staple cartridge (140) and actuate the staple drivers upwardly to thereby drive (or "fire") staples from cartridge (130) into tissue clamped between staple cartridge (140) and anvil plate (72). A center beam (122) is coupled with side beams (118) via a bridge member (124) (or "knife block") spaced distally from slide block (112). Center beam (122) terminates distally in a distally angled knife member (126) having a distal cutting edge (128) configured to cut tissue clamped between the distal portions of stapler halves (12, 14).

Each actuator (114, 116) of firing assembly (110) is configured and rotatable relative to slide block (112) between a deployed position and a retracted position such that only one actuator (114, 116) may be deployed at a time, for example as disclosed in U.S. Pat. No. 10,898,187, incorporated by reference above. In the deployed position, an actuator (114, 116) may be driven distally by an operator to actuate firing assembly (110) distally through stapler (10) and thereby simultaneously cut and staple tissue clamped between stapler halves (12, 14).

B. Illustrative Use of Linear Surgical Stapler

Figure 5:
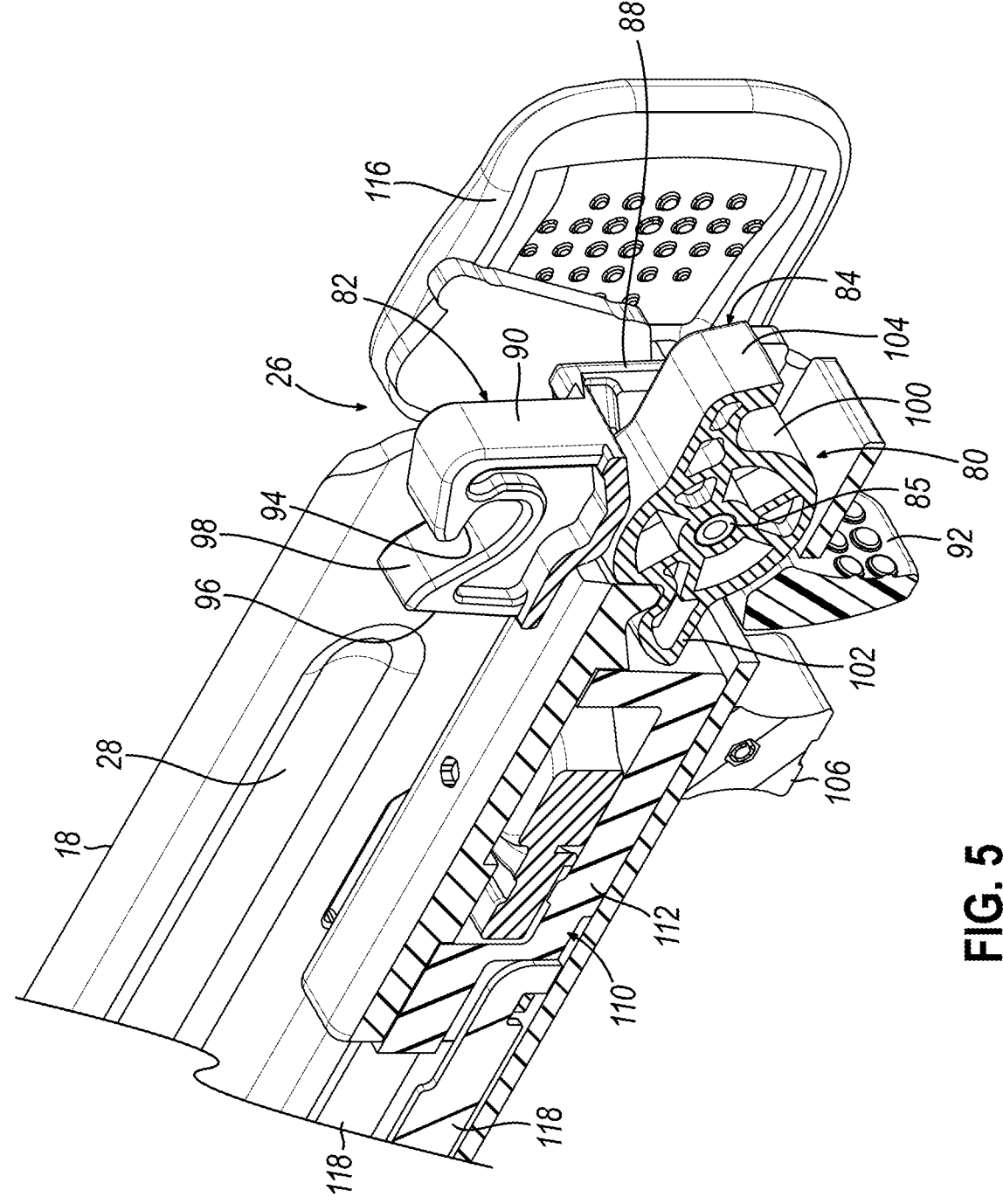
FIG. 5 depicts a cross-sectional perspective view of a proximal portion of the cartridge half of the linear surgical stapler of FIG. 1 with the clamp lever in an open position to reveal details of a firing assembly and a retaining assembly of the cartridge half.
Figure 6:
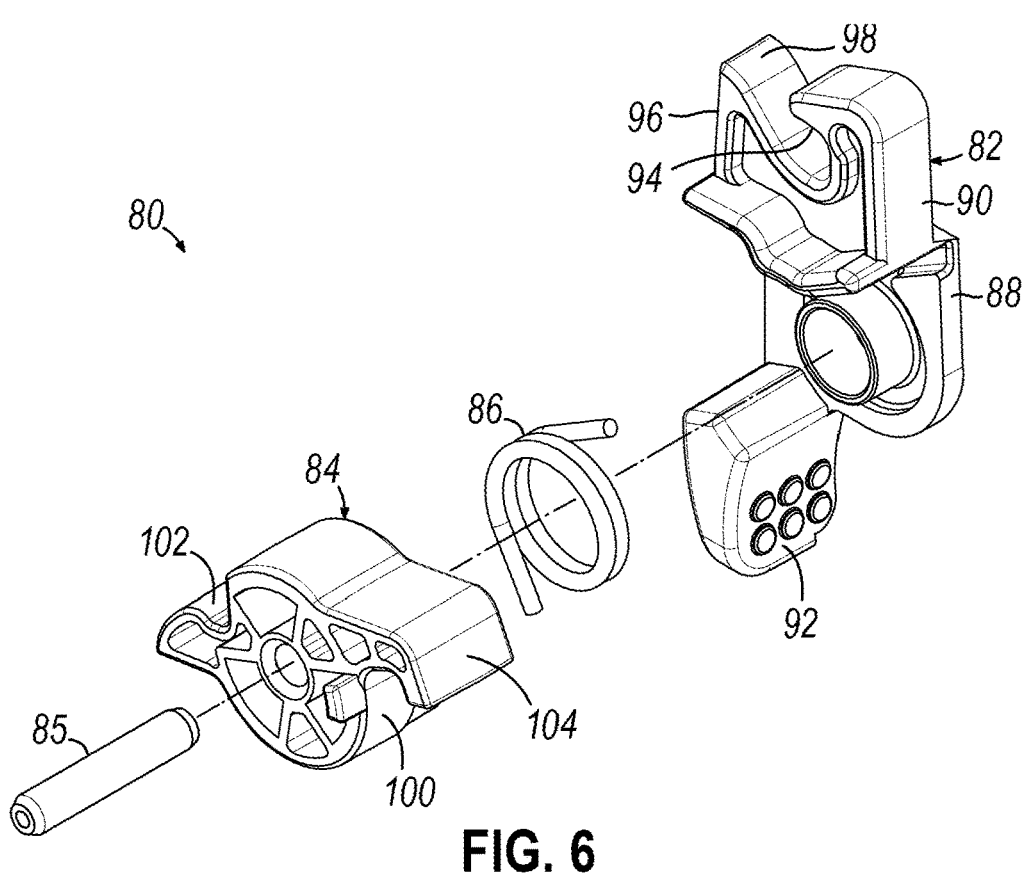
FIG. 6 depicts an exploded perspective view of the retaining assembly of FIG. 5.
Figure 7:
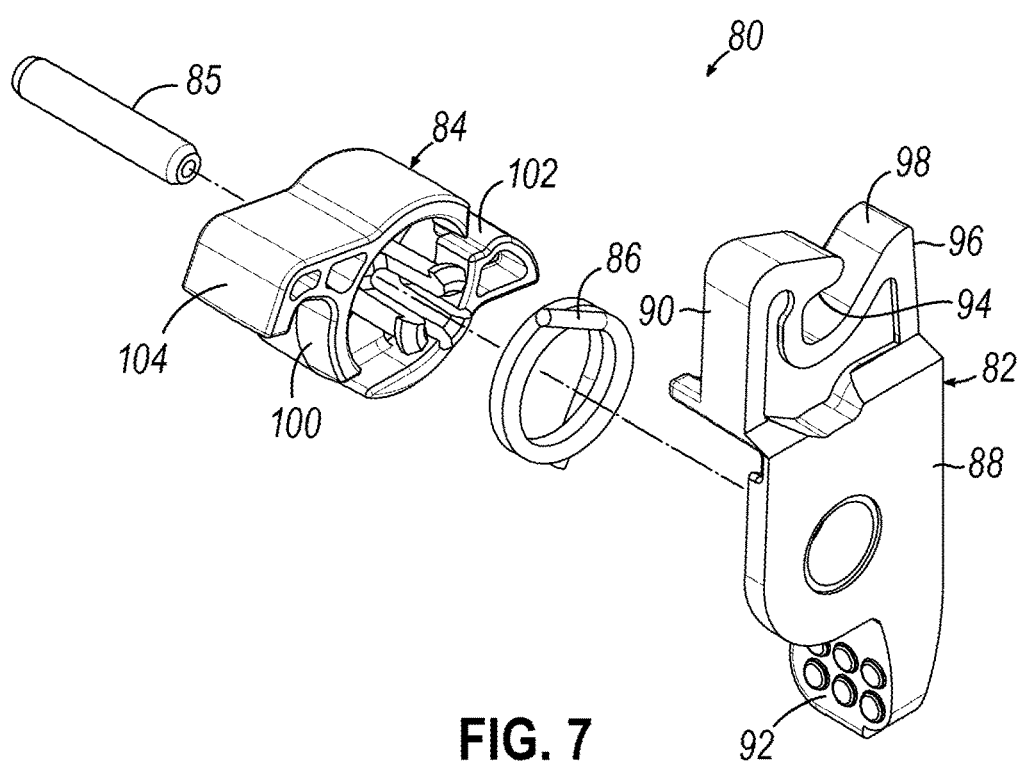
FIG. 7 depicts another exploded perspective view of the retaining assembly of FIG. 5.

FIGS. 9A-9E show illustrative coupling of stapler halves (12, 14) and subsequent firing of assembled stapler (10) during a surgical procedure. As shown in FIG. 9A, clamp lever (40) of cartridge half (12) is provided in the open position so that jaw slots (50) align with vertical slots (24) of cartridge channel side flanges (22). Additionally, firing assembly (110) is maintained in its proximal home position by detent member (84) of retaining assembly (80), as shown in FIG. 5 described above. At this stage, a section of tissue (not shown) to be stapled and cut may be positioned over the top of staple cartridge (140) disposed in distal jaw portion (20) of cartridge half (12). Alternatively, the tissue may be positioned over staple cartridge (140) following coupling of the proximal ends of stapler halves (12, 14), described below.

As shown in FIGS. 9A-9B, the proximal ends of stapler halves (12, 14) are aligned with one another, and proximal anvil pin (70) is directed downwardly into proximal tapered notches (26) of cartridge channel (16) to engage latch finger (90) of anvil latch member (82). This engagement forces anvil latch member (82) to resiliently rotate clockwise, thus enabling latch finger (90) to capture anvil pin (70) and thereby releasably couple together the proximal ends of stapler halves (12, 14), as seen in FIG. 9B. With clamp lever (40) still in the open position as shown in FIG. 9B, stapler (10) is provided in a "hang-open" state such that stapler (10) may be held single-handedly by anvil half (14) while cartridge half (12) remains coupled to anvil half (14). As shown in FIG. 9C, and with clamp lever (40) remaining in the open position, anvil half (14) is rotated toward anvil half (14) about proximal anvil pin (70) so that distal latch pin (68) of anvil half (14) is received into vertical slots (24) of cartridge channel side flanges (22) and jaw slots (50) of clamp lever (40). Distal jaw portions (20, 64) of stapler halves (12, 14) are now in a partially approximated state such that tissue received therebetween may be finally adjusted before clamping.

As shown in FIG. 9D, clamp lever (40) is closed to draw anvil latch pin (68) against the closed proximal ends of jaw slots (50) and thereby fully clamp anvil half (14) against cartridge half (12), with tissue (not shown) clamped between the stapling surfaces defined by staple cartridge (140) and anvil plate (72). A slight transverse gap is defined between staple cartridge (140) and anvil plate (72) by a tissue gap post (162) of staple cartridge (140), thus accommodating the tissue therebetween with a predetermined degree of tissue compression. As shown in FIGS. 9A and 9B, tissue gap post (162) is disposed at a distal end of staple cartridge (140) and is configured to contact a distal end of anvil plate (72) when stapler (10) is in the fully clamped state shown in FIG. 9D. In response to clamp lever (40) reaching the fully closed position, clamp lever latch member (54) may rotate to capture a proximal end of a base wall of cartridge channel (16) and thereby assume a latched state in which clamp lever latch member (54) maintains clamp lever (40) in the closed position.

Figure 9E:
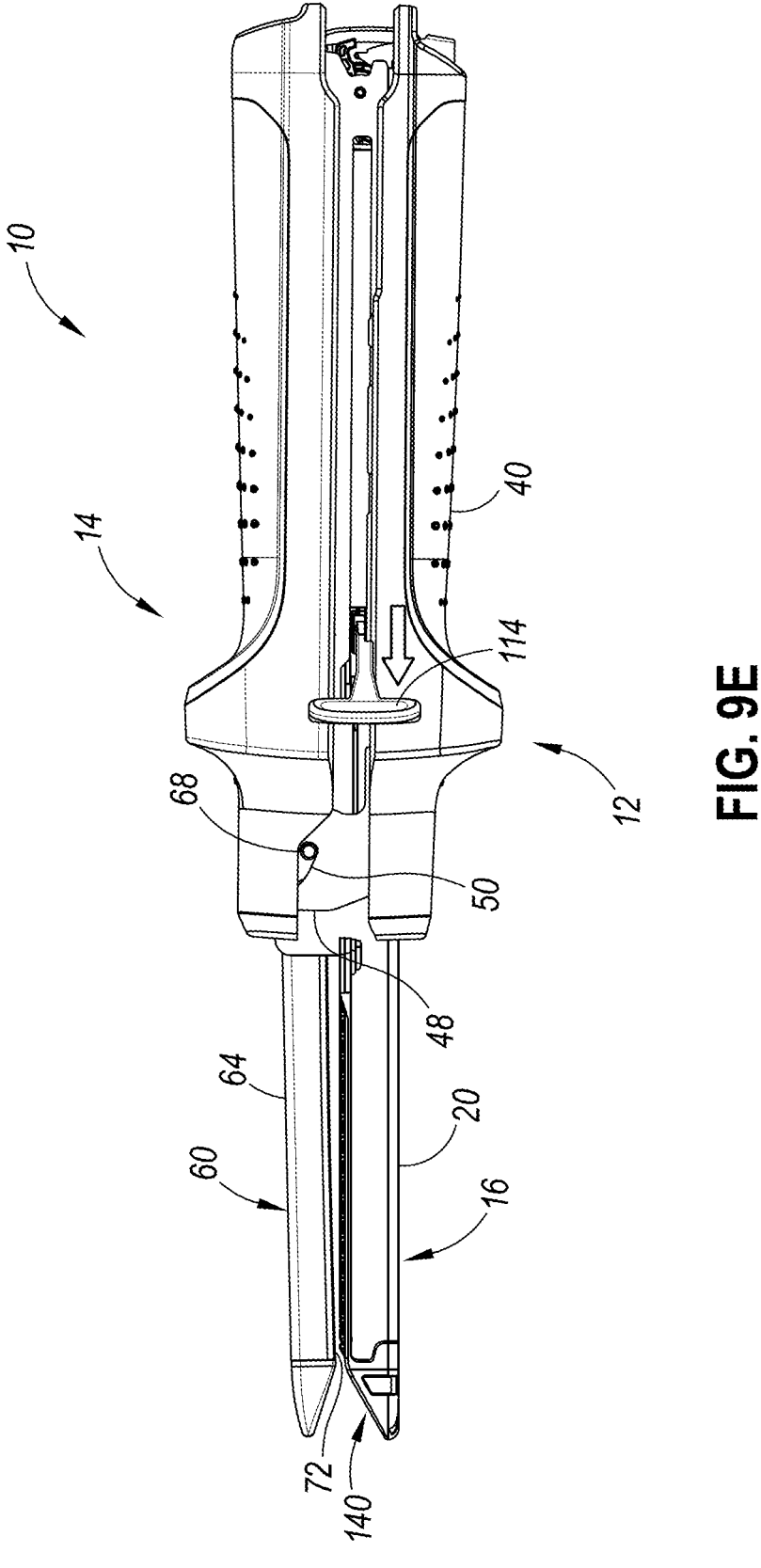
FIG. 9E depicts a side elevational view of the linear surgical stapler of FIG. 1, showing distal actuation of the firing assembly while the stapler halves are in the fully clamped state.

As shown in FIG. 9E, upon reaching the fully clamped state, stapler (10) may be fired by driving a deployed actuator (114, 116) of firing assembly (110) distally along proximal frame portion (18) of cartridge half (12). This action causes elongate beams (118, 122) of firing assembly (110) to translate distally through corresponding channels formed in staple cartridge (140) and thereby fire staples into the clamped tissue via cam ramps (120) and staple drivers (172), and simultaneously cut the clamped tissue with knife member (126). Following completion of the firing stroke, firing assembly (110) is returned to its proximal home position via the actuator (114, 116). Clamp lever latch member (54) may then be depressed to release the proximal end of clamp lever (40) from cartridge channel (16), thus permitting clamp lever (40) to be re-opened. Then, release button (92) of retaining assembly (80) may be depressed to release anvil half (14) from cartridge half (12) so that stapler halves (12, 14) may be separated from one another, thereby releasing the newly stapled and severed tissue. It will be understood that in some versions, stapler (10) may include additional features to promote decoupling of stapler halves (12, 14), for example as disclosed in U.S. Pat. No. 11,033, 266, incorporated by reference above.

II. ILLUSTRATIVE CLAMPING LOCKOUTS

As described above, when latch pin (68) of linear surgical stapler (10) is properly aligned with jaw slots (50), actuation of clamp lever (40) from the open position to the closed position (see FIG. 9C-9D) operates to cammingly drive the opposed lateral ends of latch pin (68) proximally within jaw slots (50) and thereby clamp stapler halves (12, 14) together to approximate stapling surfaces (72, 140). In the fully closed position of clamp lever (40), latch member (54) is configured to releasably engage the proximal end of cartridge channel frame portion (18) and thereby retain clamp lever (40) in the fully closed position.

In some instances, it may be difficult for the surgeon to sufficiently approximate stapler halves (12, 14) to properly align latch pin (68) with jaw slots (50), such as when clamping on thick tissue, and the surgeon may unknowingly close clamp lever (40) without properly capturing latch pin (68), such that stapler halves (12, 14) are not properly latched together. Accordingly, it may be desirable configure stapler (10) to inhibit closure and/or latching of clamp lever (40) to thereby provide a clear indication to the surgeon when latch pin (68) has not been properly captured within jaw slots (50), and that readjustment of clamp lever (40) or stapler halves (12, 14) is required to achieve proper clamping on tissue. FIGS. 10-18 and FIGS. 19-22D show illustrative versions of such configurations, as described in greater detail below.

A. Clamping Lockout Having Housing and Pivotable Arm

FIGS. 10-18 show an illustrative linear surgical stapler assembly (200) that incorporates linear surgical stapler (10) fitted with an illustrative clamping lockout in the form of an interlock assembly (202). Interlock assembly (202) is configured to inhibit latching of clamp lever latch member (54) of clamp lever (40) to proximal frame portion (18) of cartridge half (12) when latch pin (68) of anvil half (14) is not properly aligned with and captured by clamp lever jaws (48) when clamp lever (40) is fully closed. In that regard, interlock assembly (202) is configured to function as a poka-yoke feature that protects against misuse of linear surgical stapler (10) by mitigating the risk of a user firing linear surgical stapler (10) on tissue when stapler (10) has not first been properly clamped on the tissue.

Figure 10:
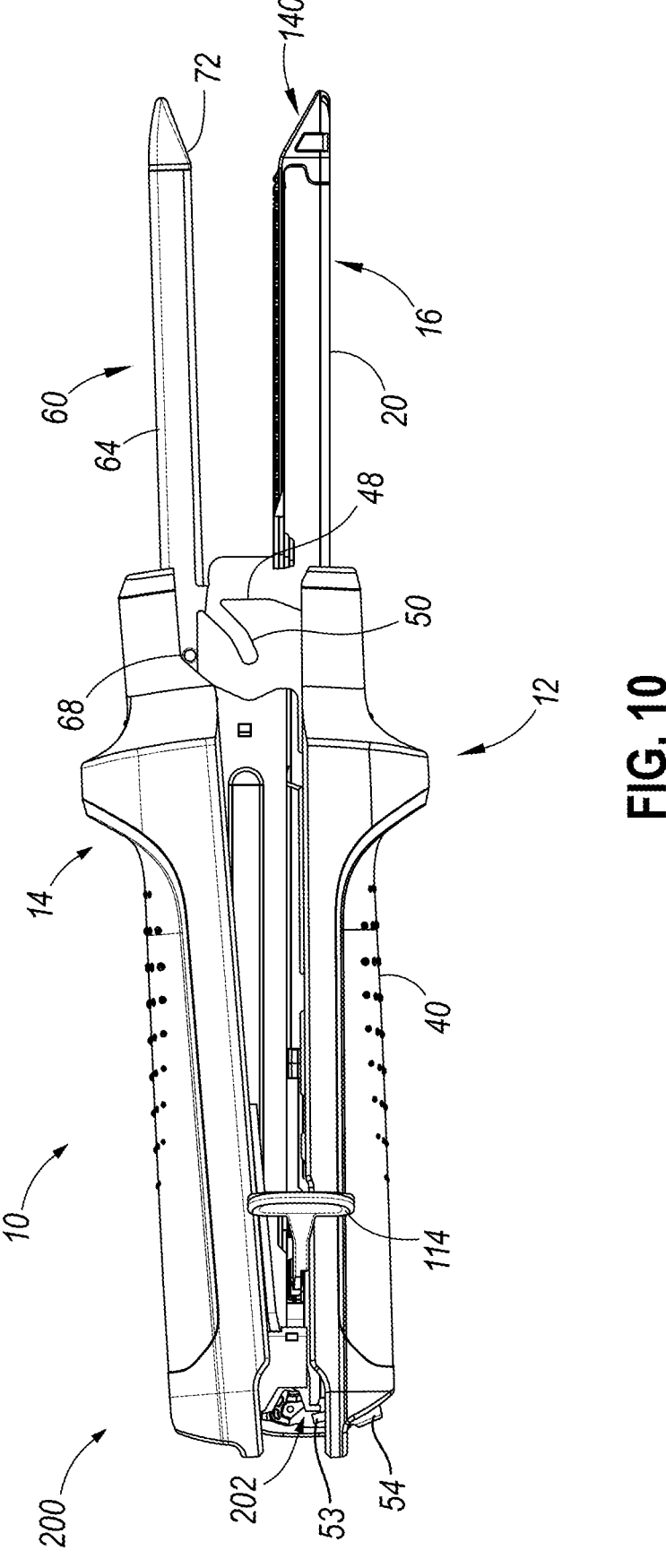
FIG. 10 depicts a side elevational view of the linear surgical stapler of FIG. 1 fitted with an interlock assembly, showing the clamp lever in a fully closed, non-latched position.
Figure 11:
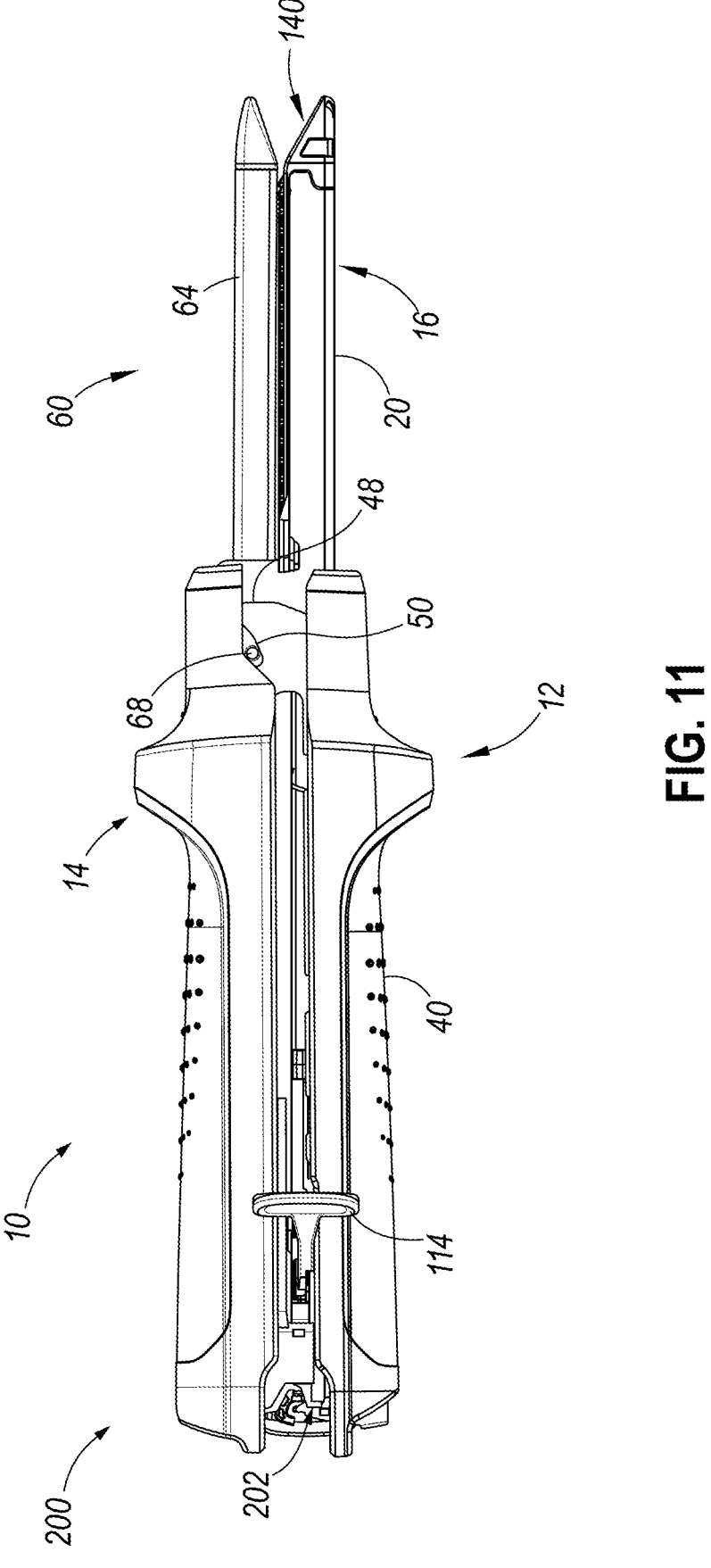
FIG. 11 shows the linear surgical stapler of FIG. 10, showing the clamp lever in a fully closed, latched position.

It should be noted that interlock assembly (202) may be backwards integrated with an existing linear surgical stapler (10) without little or no modification to linear surgical stapler (10), thus creating minimal impact upon the assembly process for linear surgical stapler (10). As described in greater detail below, when clamp lever (40) is improperly positioned by a user relative to the anvil half (14) such that clamp lever (40) in the closed position fails to properly capture latch pin (68), for example as shown in FIG. 10, interlock assembly (202) assumes a lockout state in which a proximal portion of the interlock assembly (202) engages the clamp lever latch member (54), thus preventing the clamp lever latch member (54) from assuming the latched state such that clamp lever (40) is unable to maintain the closed position. This provides a clear indication to the user that clamp lever (40) must be reopened and properly aligned with latch pin (68) to achieve proper clamping on tissue before firing. As shown in FIG. 11, when latch pin (68) is properly aligned with and captured by clamp lever (40) in the closed position, anvil half (14) engages a proximal portion of interlock assembly (202) to transition it from the lockout state to a bypass state in which the proximal portion of interlock assembly (202) disengages clamp lever latch member (54), thus permitting clamp lever latch member (54) to assume a latched state and maintain clamp lever (40) in the closed state for subsequent firing on clamped tissue.

Figure 12:
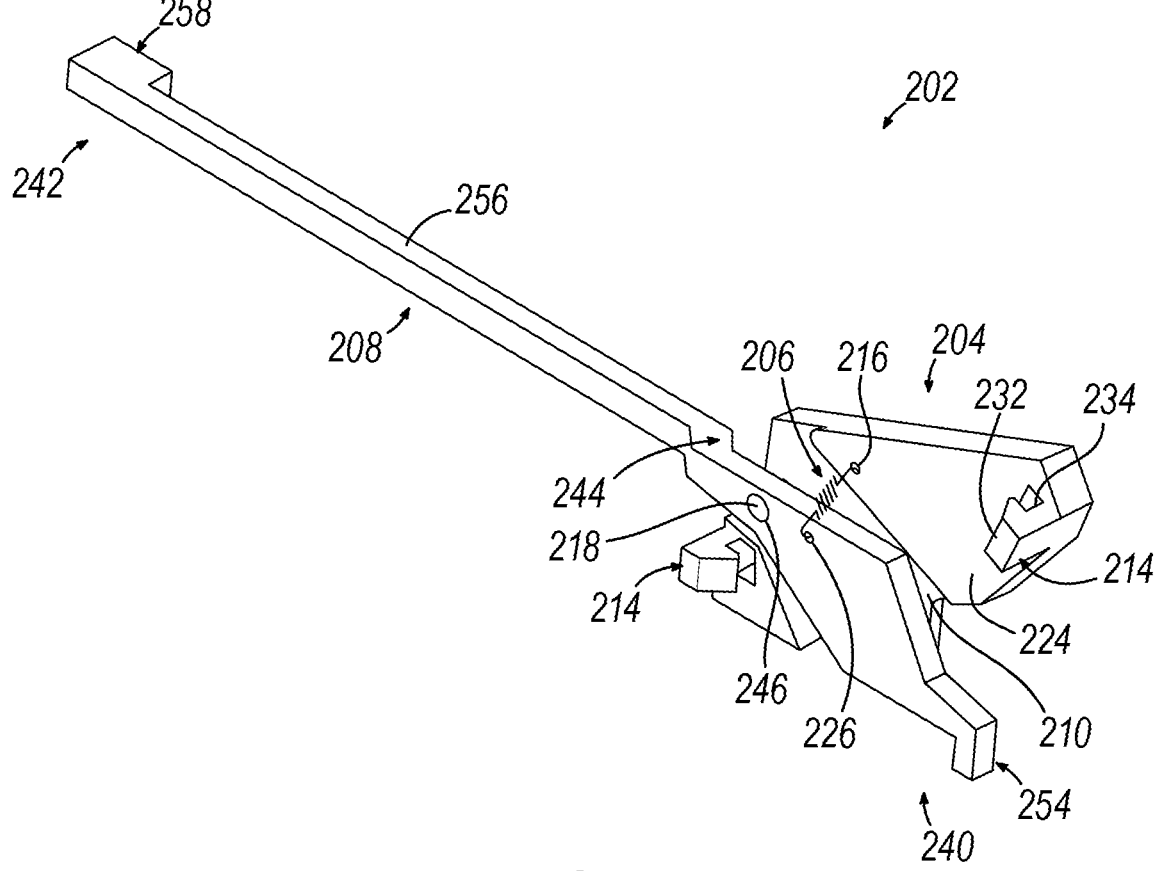
FIG. 12 depicts a perspective view of the interlock assembly of FIG. 10.

FIG. 12 shows the interlock assembly (202) including a housing (204), an elongate lockout arm (208), and a spring (206). Housing (204) and elongate arm (208) may be constructed of a polymer, plastic, or a surgically safe materials known in the art to be rigid and having a low production cost. Housing (204) and elongate arm (208) are individually formed by injection molding or additive manufacturing and are assembled together after molding. Spring (206) is fitted between housing (204) and elongate arm (208). As described in greater detail below, arm (208) is rotatable relative to housing (204) between a lockout position in which arm (208) inhibits latching of clamp lever latch member (54) to cartridge channel proximal frame portion (18), and a bypass position in which arm (208) permits latching clamp lever latch member (54) to proximal frame portion (18), and spring (206) is configured to bias arm (208) in a first rotational direction into the lockout position.

Figure 13:
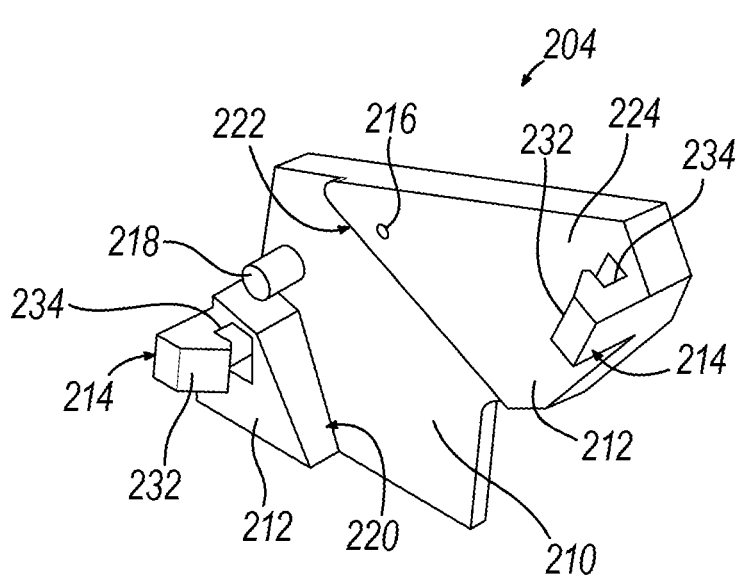
FIG. 13 depicts a perspective view of a housing of the interlock assembly of FIG. 12.

As shown in FIG. 13, housing (204) includes a recessed portion (210), a pair of raised portions (212), a pair of engagement features (214), a housing spring retainer (216), and a spindle (218). The recessed portion (210) is positioned between raised portions (212). Raised portions (212) are generally planar and include a first inner portion (220), a second inner portion (222), and a top portion (224). Top portion (224) is configured to fit flush against the proximal end of a side flange (22) of the cartridge channel (16). Inner portions (220) define the recessed portion (210) and extend transversely between top portions (224) and recessed portions (210). First and second inner portions (220, 222) are configured to engage a portion of elongate arm (208) to limit the range of angular motion of elongate arm (208). One of the raised portions (212) includes a spring retainer in the form of a spring aperture (216) configured to retain an end of spring (206) to housing (204). An engagement feature (214) is positioned upon each top portion (224). Each engagement feature (214) includes an angled portion (232) and a straight portion (234). Each engagement feature (214) is configured to irremovably affix housing (204) to a side flange (22) of cartridge channel (16). Spindle (218) extends transversely from recessed portion (210) and is configured to rotatably couple with and support elongate arm (208).

Figure 14:
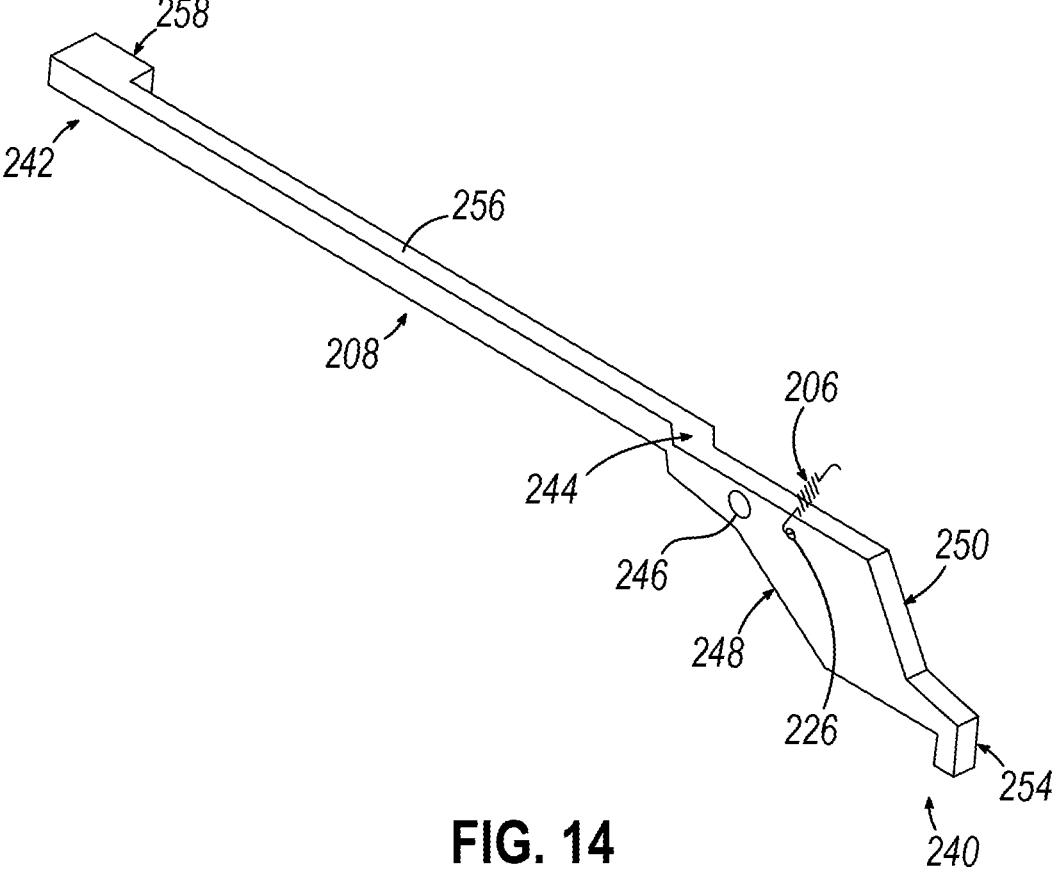
FIG. 14 depicts a perspective view of a lockout arm of the interlock assembly of FIG. 12.

FIG. 14 shows the elongate arm (208) and spring (206). Elongate arm (208) includes a proximal portion (240) and a distal portion (242). Distal portion (242) is slightly offset from proximal portion (240) at an intermediate portion (244) to accommodate clearances when elongate arm (208) rotates within linear surgical stapler (10). Proximal portion (240) includes a pin bore (246), a first angled surface (248), a second angled surface (250), a spring bore (226), and a proximal tab (254). Spring bore (226) is configured to accept an end of spring (206) opposite the end that is captured by spring aperture (216) to rotatably bias elongate arm (208) in a first direction toward its lockout position. Spring (206) may include a compression spring, a tension spring, a torsion spring, or a spiral spring, for example. In the present example, spring (206) is shown in the form of a compression spring that is secured to the elongate arm (208) within spring bore (226) and the other end of tension spring is secured a spring aperture (216) positioned on housing (204) (see FIG. 12). In versions using a torsion or spiral spring, spring bore (226) may be positioned proximal to pin bore (246) and spring aperture (216) may also be defined by recessed portion (210) rather than one of raised portions (212).

Pin bore (246) is sized and configured to be rotatably coupled with the spindle (218). First angled surface (248) is configured to engage a first inner portion (220) to limit the freedom of travel of the elongate arm (208) in a first angular direction. A second angled surface (250) is configured to limit the freedom of travel of elongate arm (208) in a second angular direction. Proximal tab (254) extends transversely downwardly relative to the pin bore (246) and is aligned with edge of proximal portion (240). Proximal tab (254) is configured to engage clamp lever latch member (54) when arm (208) is in the lockout position, as described below.

Distal portion (242) of arm (208) includes an elongate member (256) that extends distally and terminates at a distal tab (258). Elongate member (256) is not limited to rectangular or square cross-sections as shown. Elongate member (256) may include a circular or hollow profile, for example. Distal tab (258) extends transversely downwardly from elongate member (256) and is configured to engage a portion of anvil shroud (78) when stapler halves (12, 14) are properly clamped together with clamp lever (40) in the closed position.

Figure 15:
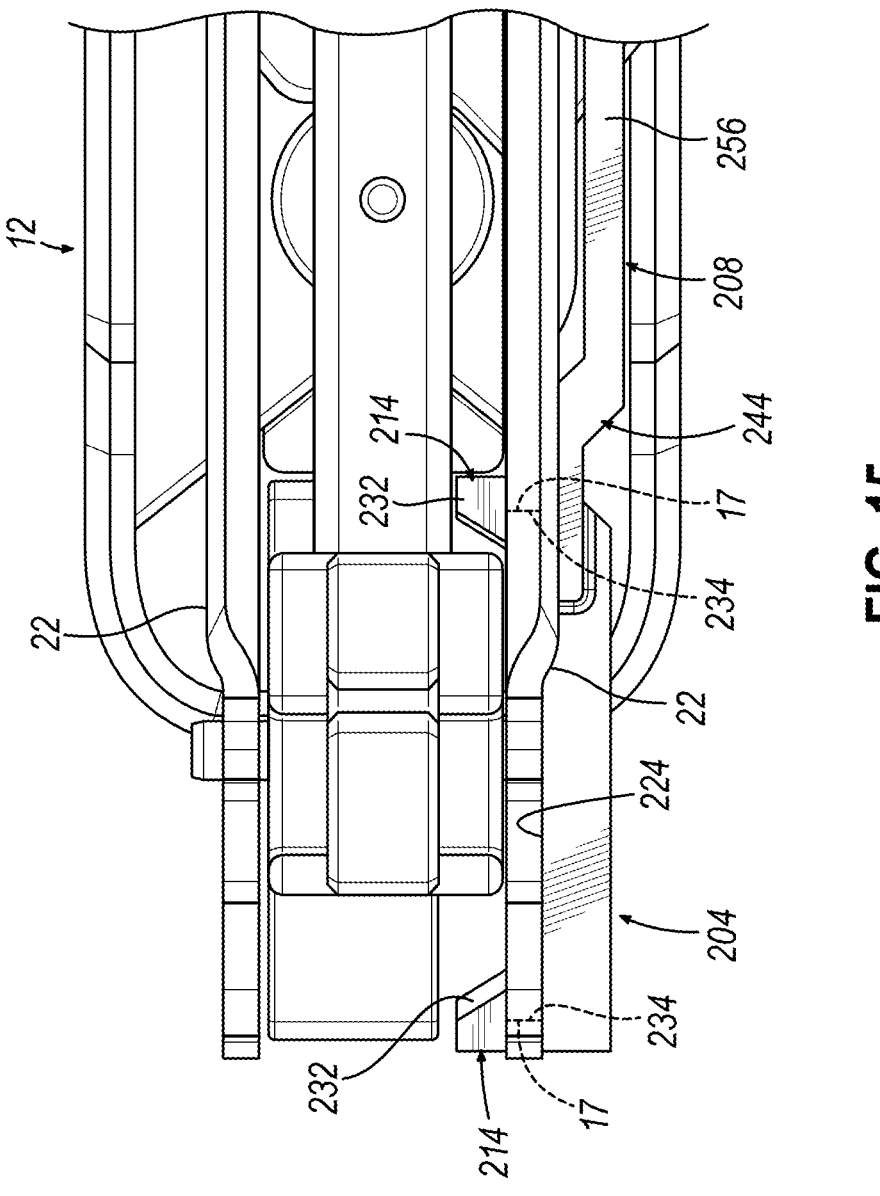
FIG. 15 depicts an enlarged top elevational view of the linear surgical stapler of FIG. 1 with the interlock assembly installed within the linear surgical stapler.

FIG. 15 shows each engagement feature (214) of housing (204) affixed to the proximal end of a side flange (22) of cartridge channel (16) through a pair of channel apertures (17). As shown in FIGS. 15-16B, cartridge channel (16) includes a pair of pre-existing channel apertures (17). It should be noted that two or more engagement features (214) may be used to secure the housing (204) to the cartridge channel (16). Each engagement feature (214) is configured to extend through channel apertures (17) and irremovably secure housing (204) to cartridge channel (16). Angled portion (232) is positioned more distal relative to top portion (224) than straight portion (234). Engagement feature (214) is resiliently biased to a straight configuration and is offset to an interior side of each channel aperture (17). Engagement feature (214) is inserted from a first side of channel aperture (17) to a second side of channel aperture (17). Angled portion (232) is configured to ride upon channel aperture (17) deflecting engagement feature (214) away from the interior side of each channel aperture (17) in a deflected configuration until the angled portion (232) passes through channel aperture (17) to the second side of channel aperture (17). Engagement feature (214) snaps back into the straight configuration from a deflected configuration. Angled portion (232) remains on a second side of channel aperture (17).

Figure 16A:
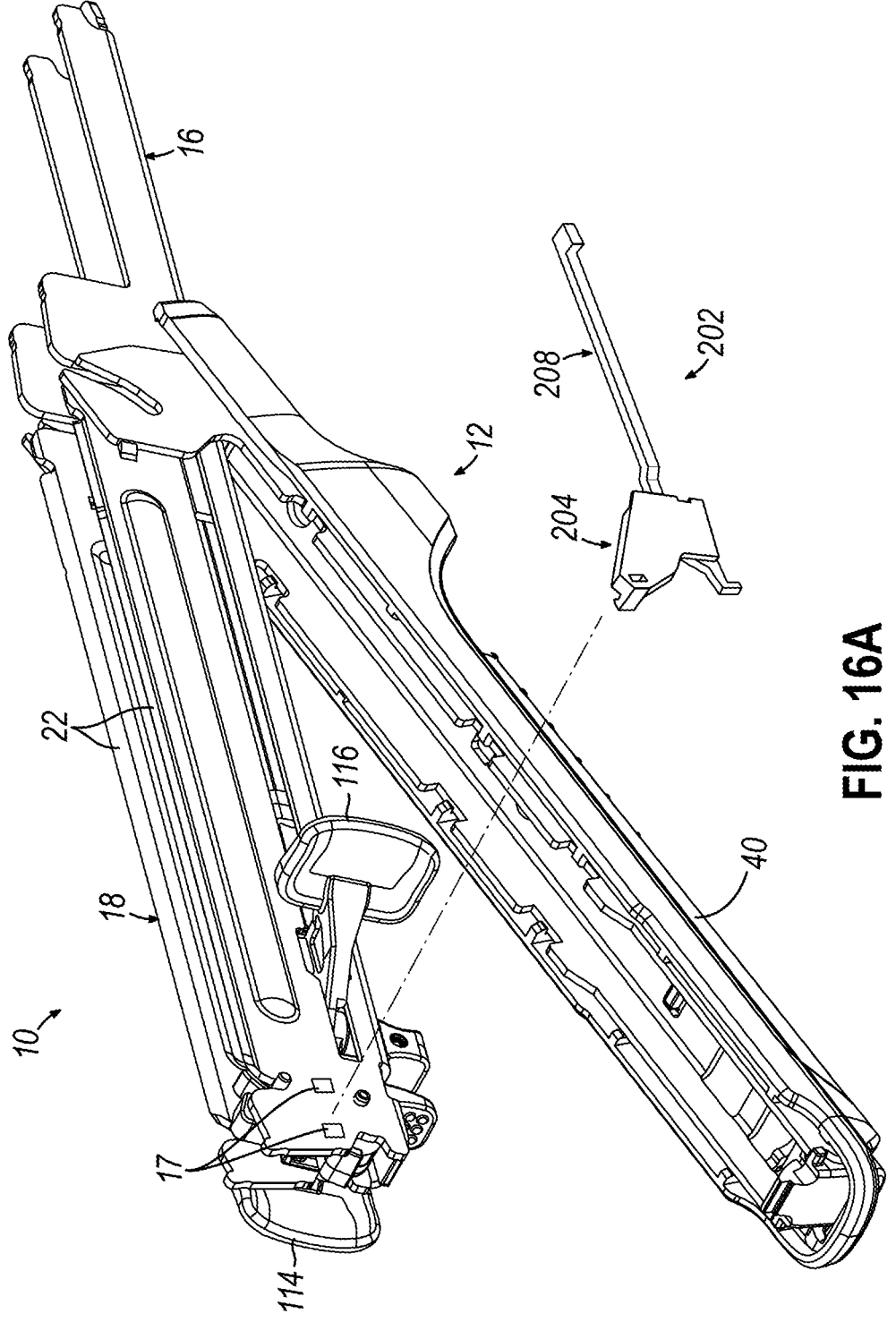
FIG. 16A depicts a perspective view of a cartridge half of the linear surgical stapler of FIG. 10, showing with interlock assembly uninstalled and spaced apart from the cartridge half.
Figure 16B:
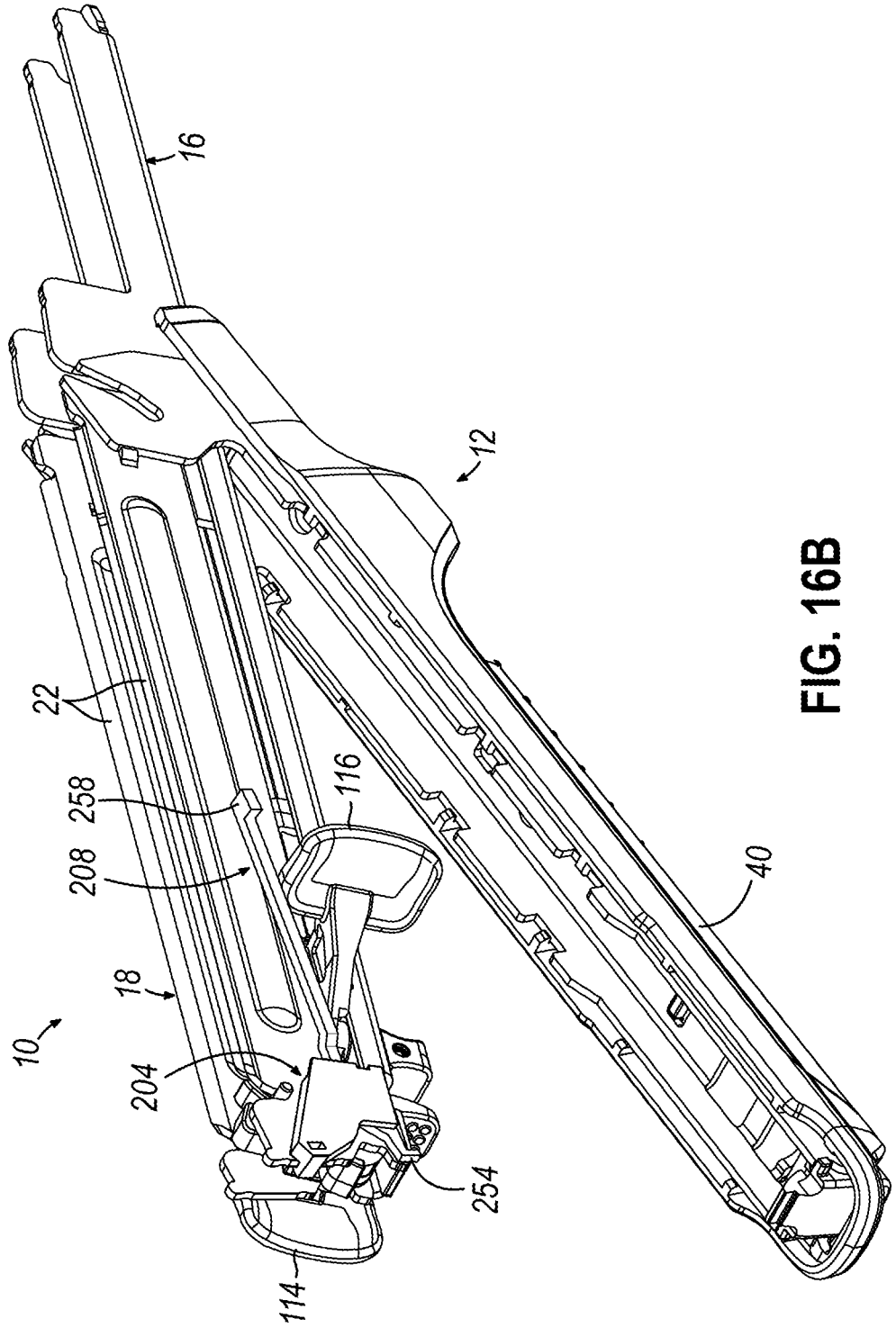
FIG. 16B depicts a perspective view of the cartridge half of FIG. 16A, showing the interlock assembly installed within the cartridge half.

FIG. 16A shows the interlock assembly (2020) spaced apart from a portion of the linear surgical stapler (10) before assembly, and FIG. 16B shows the interlock assembly (202) after assembly with the linear surgical stapler (10).

Figure 17:
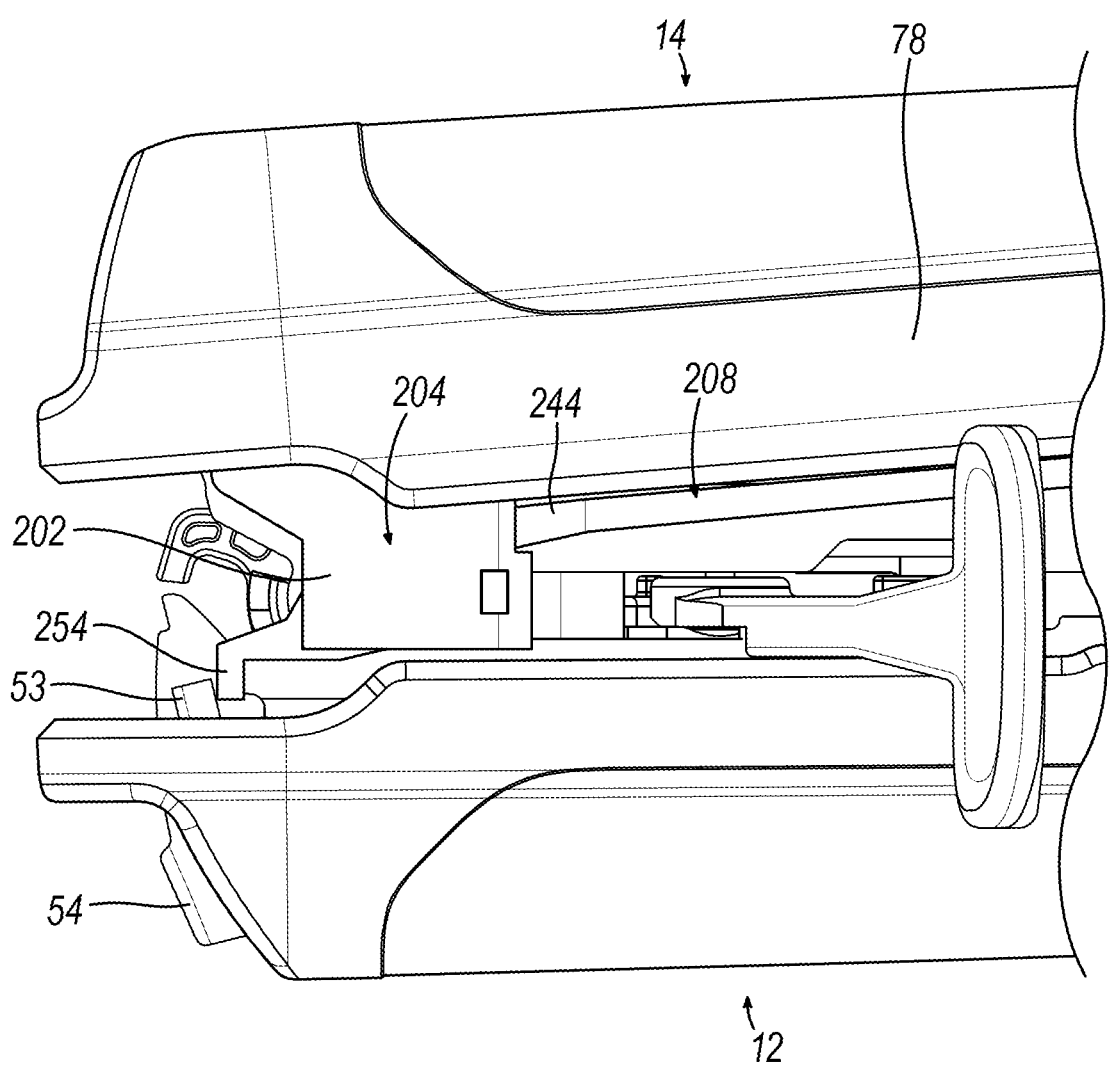
FIG. 17 depicts an enlarged side elevational view of a proximal portion of the linear surgical stapler of FIG. 10, showing the lockout arm of the interlock assembly in a lockout position and preventing a latch member of the clamp lever from fully closing.

FIG. 17 shows interlock assembly (202) preventing the clamp lever latch member (54) from rotating to capture a proximal end of a base wall of cartridge channel (16), thereby preventing the clamp lever (40) from maintaining the closed position when clamp lever (40) has failed to properly capture latch pin (68). More specifically, elongate arm (208) remains rotated about spindle (218) via the bias of spring (206) such that proximal tab (254) directly contacts and urges lateral projection (53) of clamp lever latch member (54) proximally to thereby rotate a latching portion of clamp lever latch member (54) proximally away from cartridge channel (16). As a result, clamp lever (40) fails to maintain its closed position when a user releases pressure from clamp lever (40), thus indicating to the user clamp lever (40) has not properly captured latch pin (68) and that clamp lever (40) must be reopened to achieve properly clamping of stapler (10).

The interlock assembly (202) prevents the latching of the clamp lever latch member (54) unless clamp lever (40) is actuated by the user to a full closed, latched position. By preventing clamp lever (40) from latched closed when the clamp lever (40) is in a mis-clamped state, this mitigates the risk of a user firing on tissue that has not been properly clamped, which could otherwise result in malformation of staples in the tissue.

Figure 18:
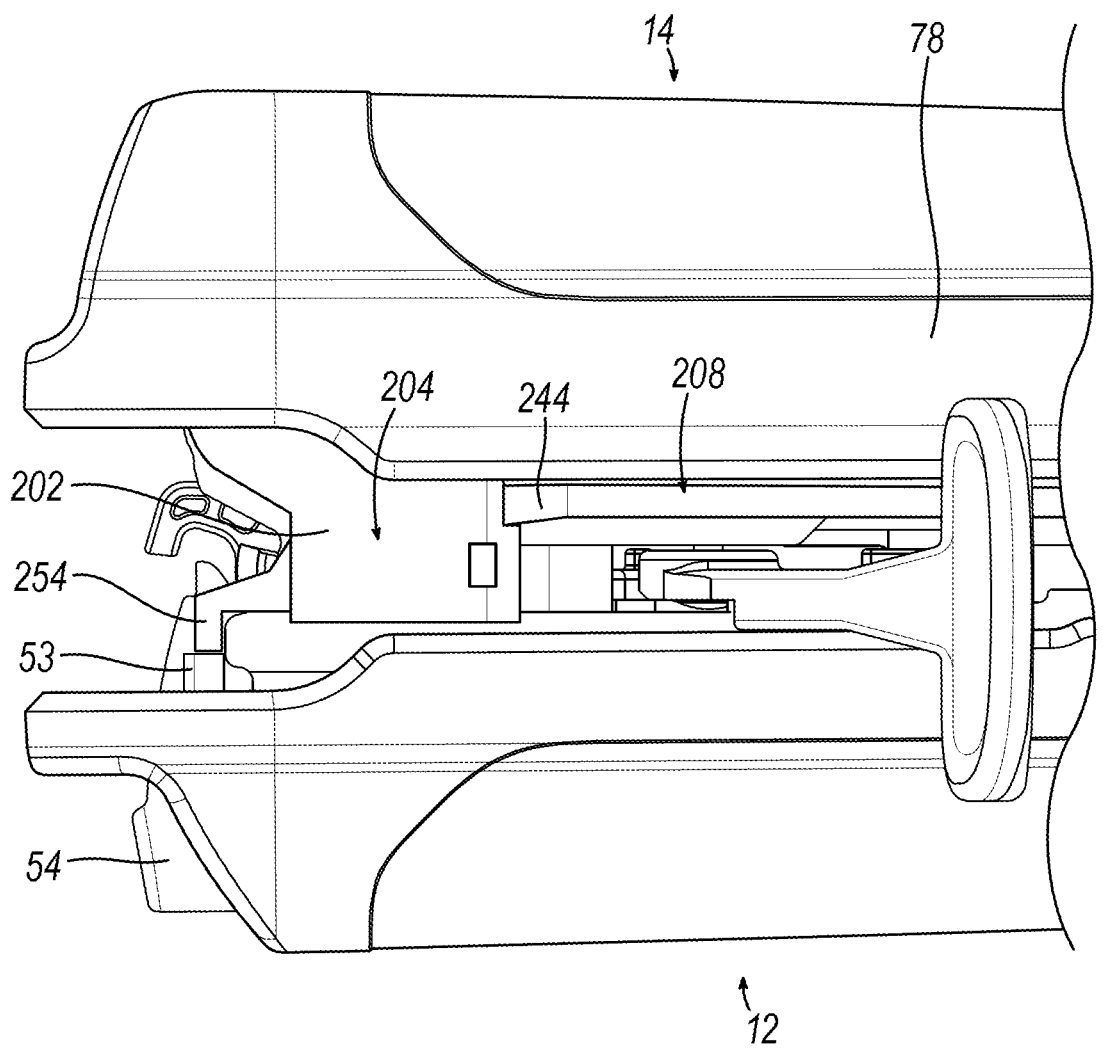
FIG. 18 depicts an enlarged side elevational view of the proximal portion of the linear surgical stapler of FIG. 17, showing the lockout arm of the interlock assembly in a bypass position and pivoted away from the clamp lever latch member.

FIG. 18 shows first and second stapler halves (12, 14) in a properly clamped state in which latch pin (68) has been properly captured by clamp lever (40) in the closed position. In this properly clamped state, anvil shroud (78) directly contacts and urges distal tab (258) of arm (208) of interlock assembly (202) downwardly against the bias of spring (206) to rotate arm (208) from its lockout position to a bypass position. In the bypass position, proximal tab (254) of arm (208) is disengaged from clamp lever latch member (54) and thus permits clamp lever latch member (54) to rotate from its unlatched position to a latched position to thereby latch the proximal end of clamp lever (40) with the proximal end of cartridge channel (16), thereby maintaining clamp lever (40) in its closed position.

B. Clamping Lockout Having Resilient Spring Arms

Figure 19:
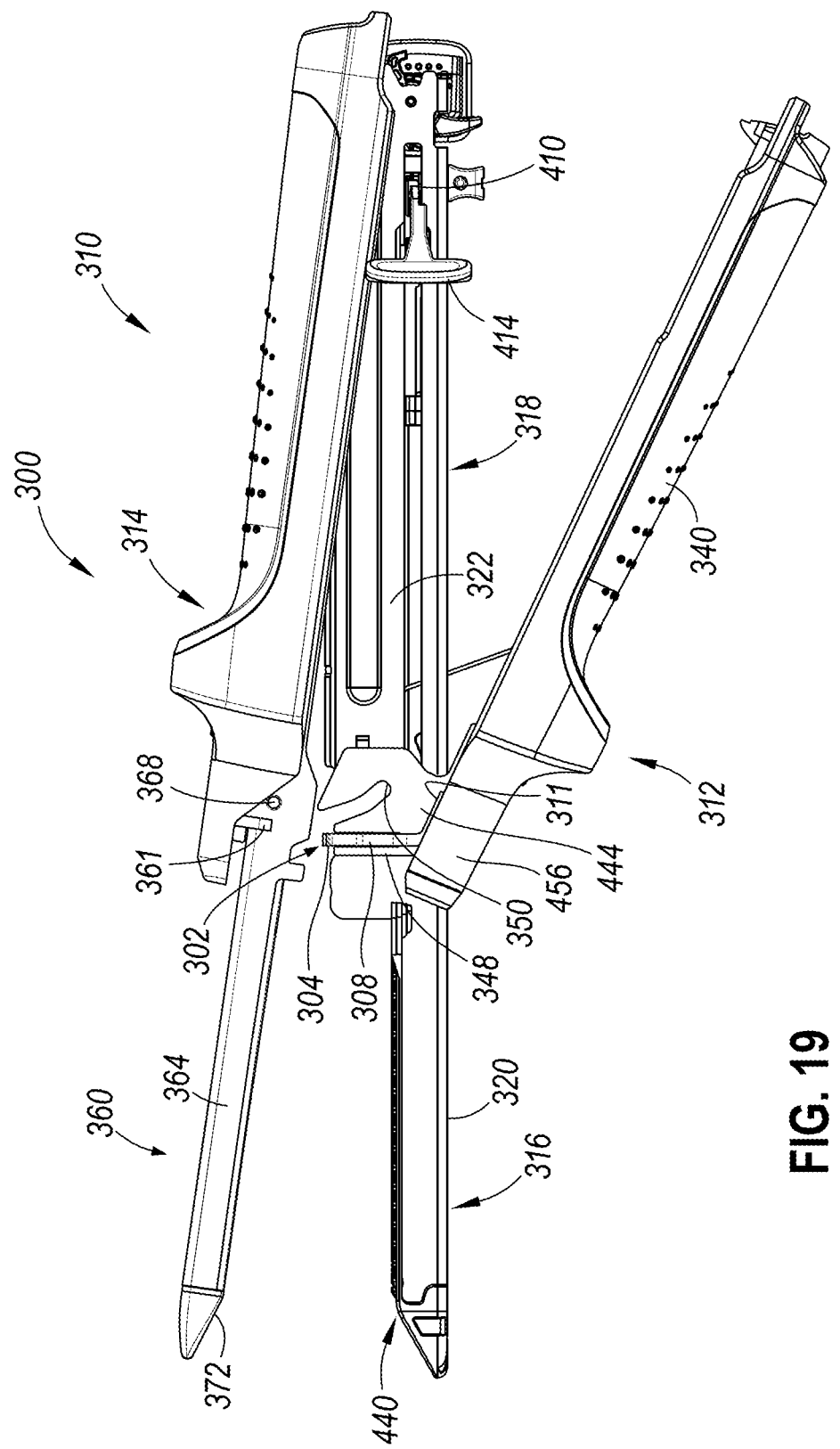
FIG. 19 depicts a side elevational view of the linear surgical stapler of FIG. 1 fitted with an interlock spring, showing the clamp lever in an open position.
Figure 20:
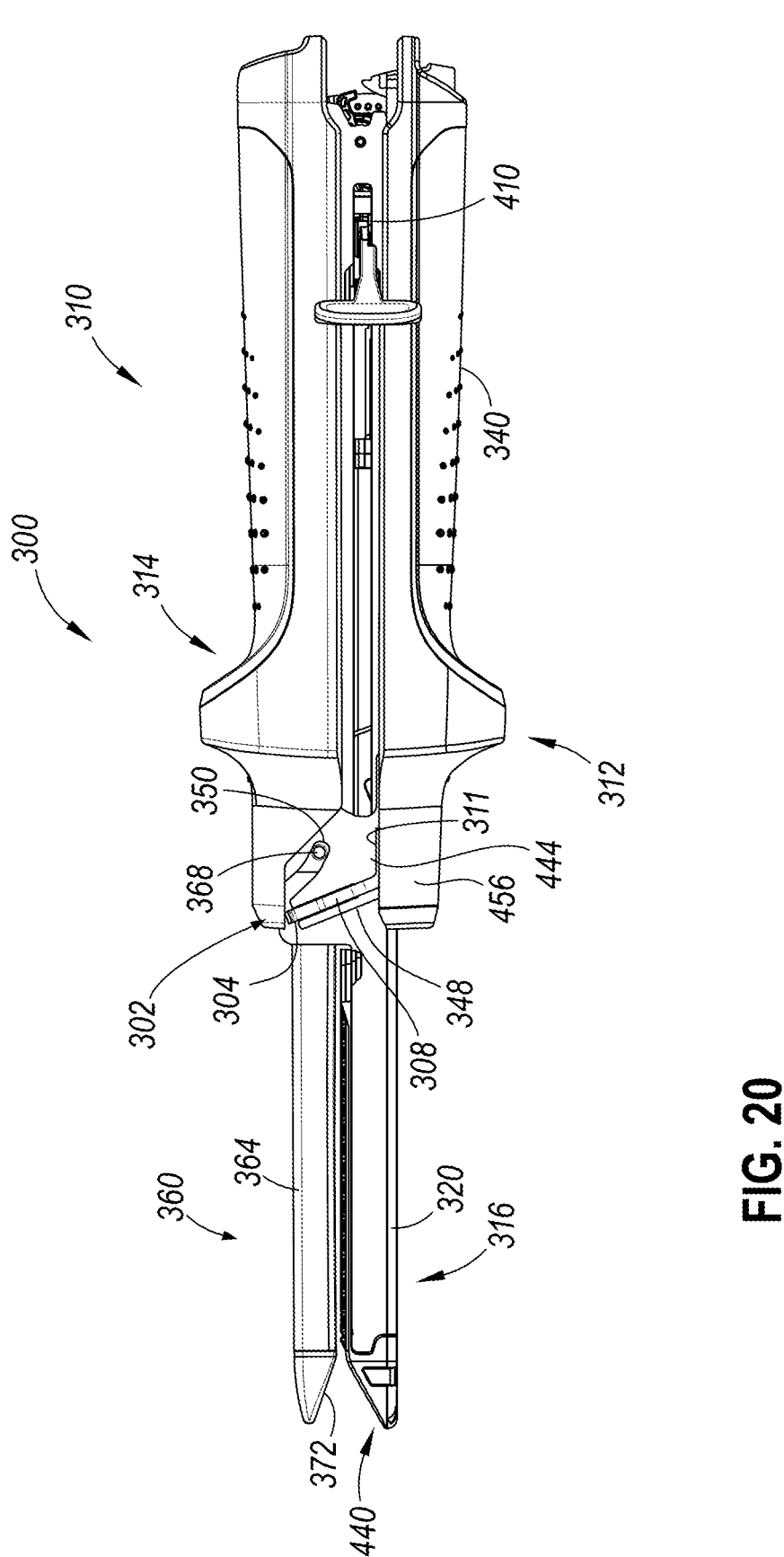
FIG. 20 depicts a side elevational view of the linear surgical stapler of FIG. 19, showing the clamp lever in a fully closed, latched position.

FIG. 19 shows another illustrative linear surgical stapler assembly (300) having a clamping lockout in the form of a resilient interlock (302) fitted within a linear surgical stapler (310), showing clamp lever (340) in the open position. Resilient interlock (302) is configured to function as a poka-yoke device configured to mistake proof linear surgical stapler (310) by inhibiting closure of clamp lever (340) from its open position unless stapler halves (312, 314) have been properly aligned with one another such that latch pin (368) is aligned with jaw slots (350) of clamp lever (340), thereby indicating to the user that stapler halves (312, 314) have yet to be sufficiently aligned properly. Accordingly, resilient interlock (302) operates to mitigate the risk of improper clamping and thus improper firing on patient tissue. In some versions interlock assembly (302) may be backwards integrated with an existing linear surgical stapler (310) with little to no modification to linear surgical stapler (310). In other versions, resilient interlock (302) may be supplied in an installed state in a new linear surgical stapler (310).

Linear surgical stapler (310) includes the same structure and arrangement as linear surgical stapler (10), except as otherwise described below. Linear surgical stapler (310) includes a clamp lever (340) having a pair of opposed jaws (348) each having a curved slot (350) with a closed proximal Jaws (348) differs from jaws (48) in that each jaw (348) defines an interlock slot (353) positioned distal of curved slot (350). Interlock slot (353) is configured to overlap and extend parallel to latch pin slot (323) of cartridge channel proximal frame portion (318) when clamp lever (340) is in the open position. As described below, each interlock slot (353) houses a respective spring arm (304, 306) of resilient interlock (302), and each latch pin slot (323) and its respective interlock slot (353) are configured to at least partially receive a respective anvil ramp (361) positioned on a respective side flange of the anvil channel of anvil half (314).

Figure 21A:
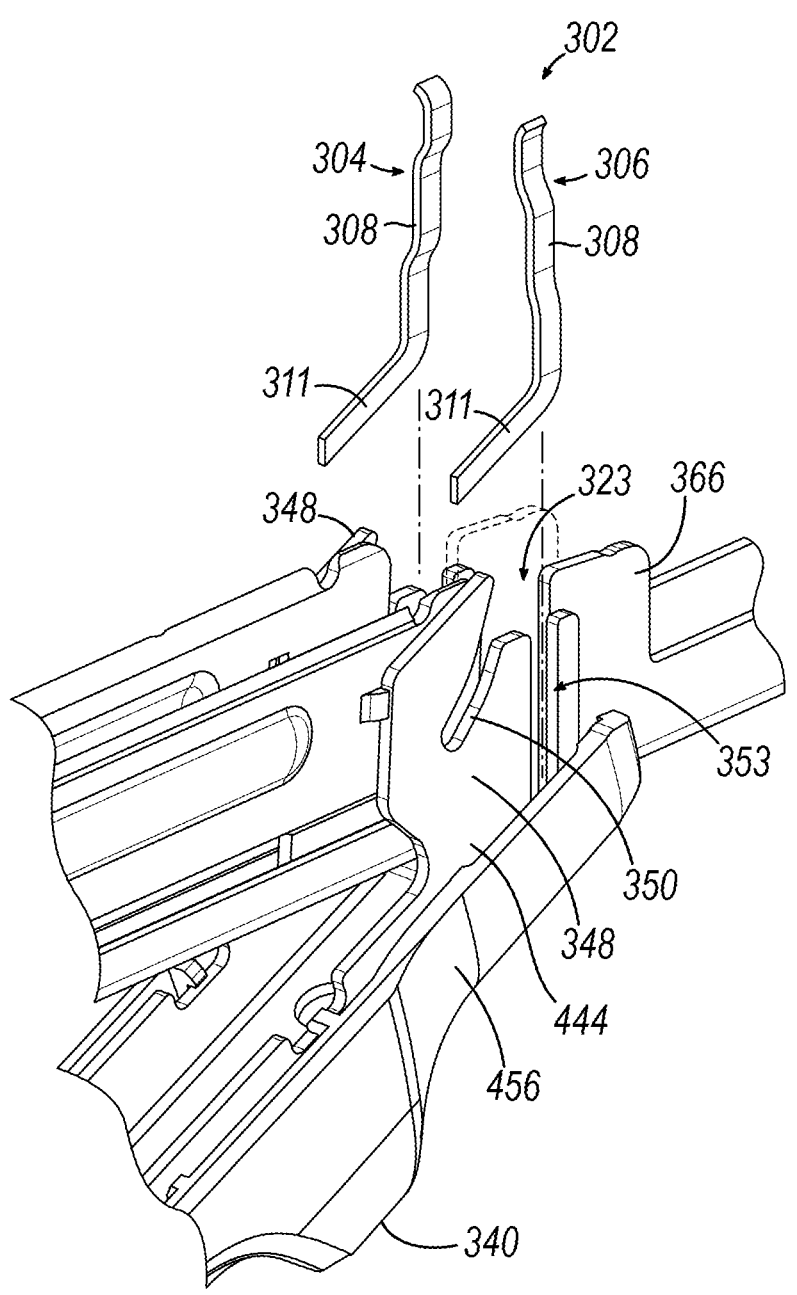
FIG. 21A depicts an enlarged perspective view of a cartridge half of the linear surgical stapler of FIG. 19, with the interlock spring shown spaced apart from the cartridge half.

FIG. 21A shows linear surgical stapler (310) with clamp lever (340) in the open position with resilient interlock (302) spaced apart from linear surgical stapler (310) and aligned with latch pin slots (323) and interlock slots (353). Resilient interlock (302) is constructed of a resilient, surgical safe material such as stainless steel or another resilient material known in the art to have resilient properties. Resilient interlock (302) includes first and second spring arms (304, 306) which may be separate or interconnected. Each spring arm (304, 306) has an upper portion (308) and a lower portion (311). Each upper portion (308) includes an inner cam surface positioned at an upper end of upper portion (308) and configured to engage the respective anvil ramp (361) of anvil half (314). Each upper portion (308) also includes an inner curved surface configured to accommodate anvil ramp (361) when clamp lever (340) is in the closed position. Each lower portion (311) extends proximally at an angle that matches the angle of the clamp lever (340) relative to the cartridge channel when clamp lever (340) is in the open position. Each lower portion (311) is configured to secure the respective spring arm (304, 306) between a lever arm and a clamp lever shroud of clamp lever (340).

Figure 21B:
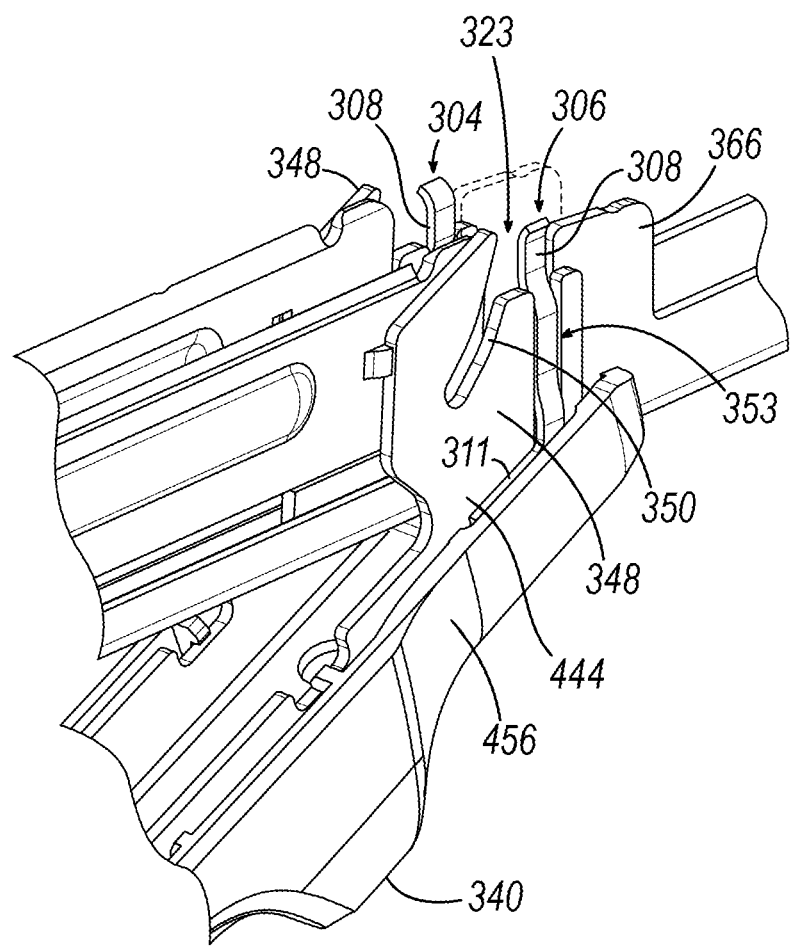
FIG. 21B depicts an enlarged perspective view of the cartridge half of FIG. 19, showing the interlock spring mounted to the cartridge half.

FIG. 21B shows linear surgical stapler (310) with clamp lever (340) in the open position with resilient interlock (302) installed within interlock slots (353). Upper portion (308) of each spring arm (304, 306) is resiliently biased laterally inwardly into the respective latch pin slot (323). When clamp lever (340) is in the open position before assembly of stapler halves (312, 314), each upper portion (308) engages the confront slot walls of the respective latch pin slot (323) and thereby locks clamp arm (340) in the open position and prevents clamp lever (340) from rotating from the open position to the closed position.

Figure 22A:
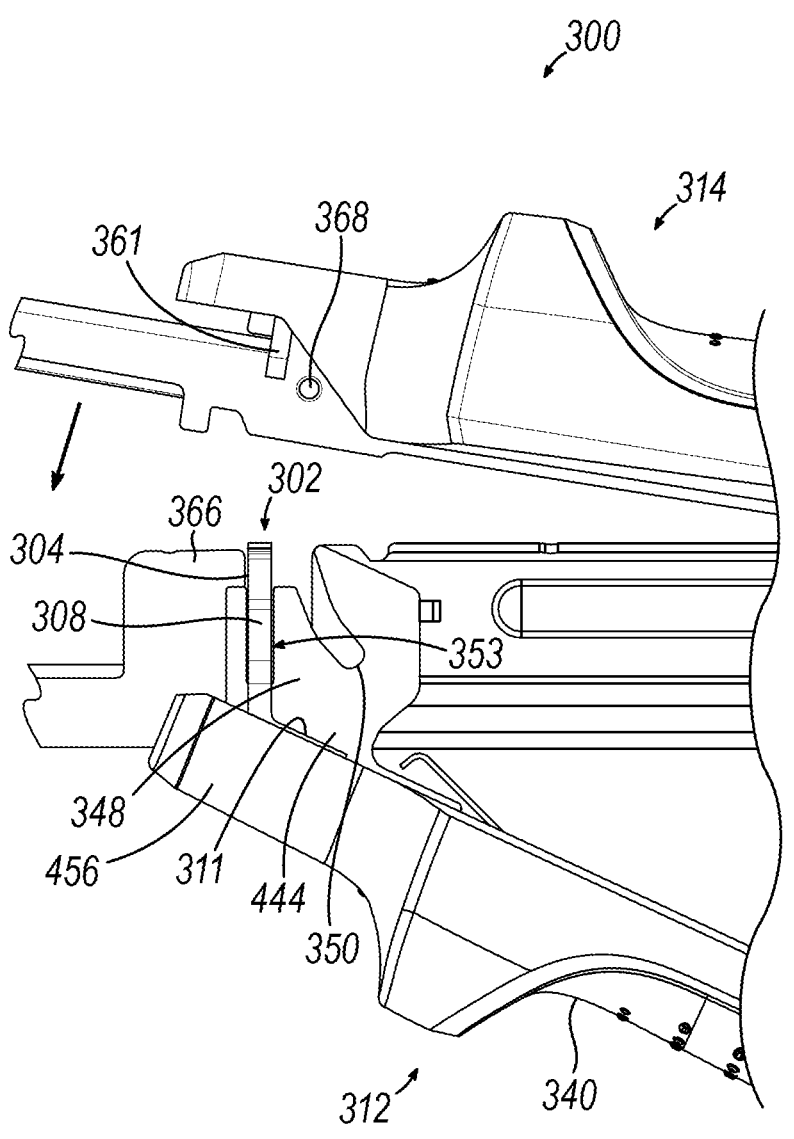
FIG. 22A depicts an enlarged side elevational view of the linear surgical stapler of FIG. 19, showing the stapler halves being approximated towards one another with the clamp lever in an open position and a ramp of the anvil half aligned with the interlock spring of the cartridge half.

FIG. 22A shows linear surgical stapler (310) fitted with resilient interlock (302). Resilient interlock (302) is positioned within ramp channel (351) with the clamp lever (340) in the open position and with anvil half (314) spaced apart from the cartridge half (312) such that resilient interlock (302) is in a lockout state in which spring arms (304, 306) are in a non-expanded, inwardly projecting state to thereby inhibit closure of clamp lever (340) in the manner described above. As shown, latch pin (368) is aligned with curved slot (350) such that anvil half (314) is properly aligned with cartridge half (312), and anvil half (314) is being approximated towards cartridge half (312).

Figure 22B:
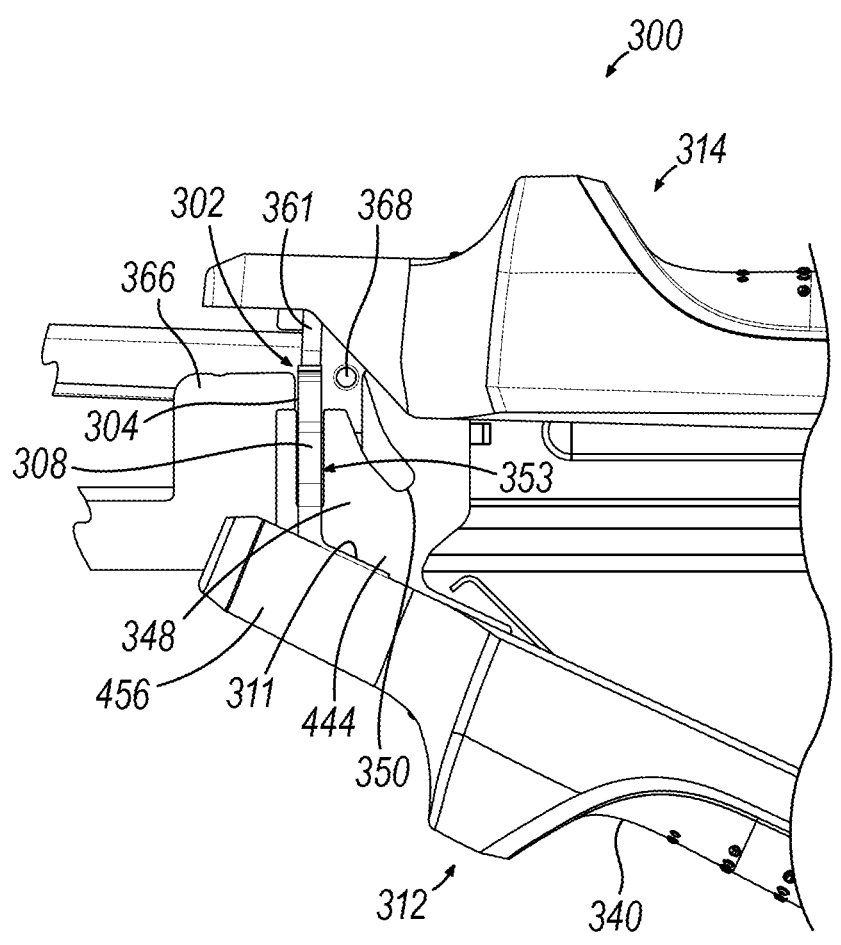
FIG. 22B depicts an enlarged side elevational view of the linear surgical stapler of FIG. 19, showing the interlock spring being initially engaged by the ramp of the anvil half while the clamp lever is in an open position.

FIG. 22B shows the linear surgical stapler (310) with anvil half (314) approximated further toward cartridge half (312) with the latch pin (368) beginning to approach an open distal end of the curved jaw slot (350). Simultaneously, upper portions (308) of spring arms (304, 306) begin to engage the respective anvil ramps (361), which cams spring arms (304, 306) laterally outwardly away from one another into a partially expanded state in which upper portions (308) are partially withdrawn laterally outwardly from latch pin slots (323) of cartridge half (312).

Figure 22C:
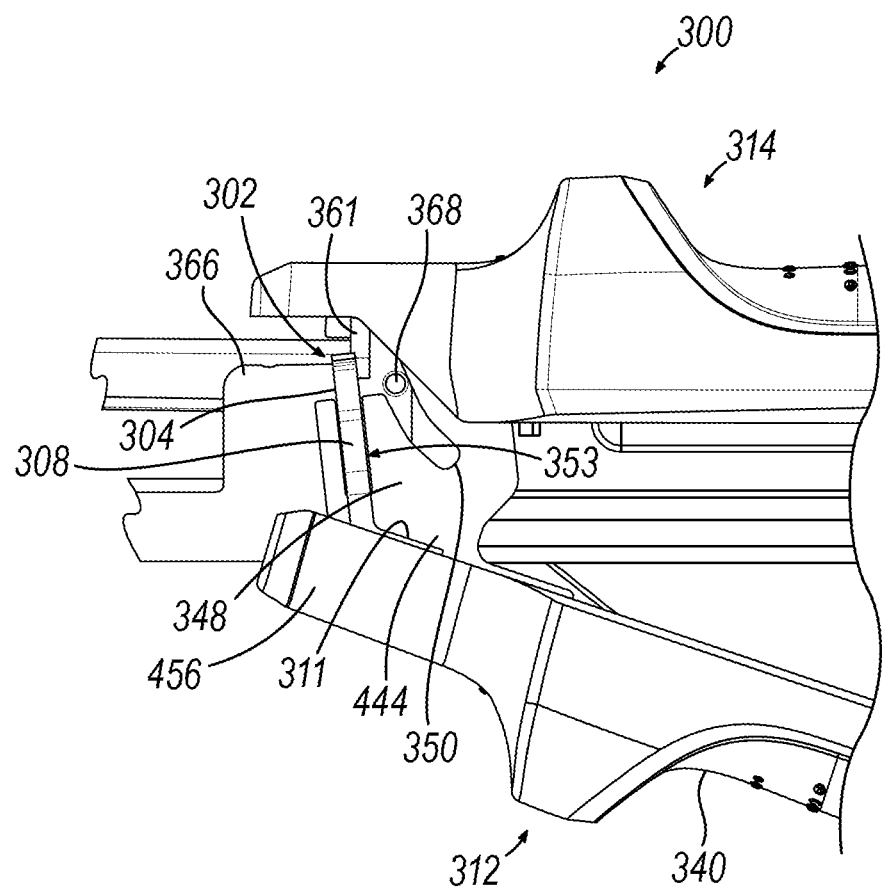
FIG. 22C depicts an enlarged side elevational view of the linear surgical stapler of FIG. 19, showing the interlock spring being spread laterally by the ramp of the anvil half as the stapler halves are approximated further via partial closure of the clamp lever from the open position toward the closed position.

FIG. 22C shows the linear surgical stapler (310) with anvil half (314) further approximated relative to cartridge half (312) with the latch pin (368) entering curved jaw slot (350). Engagement of latch pin (368) and curved jaw slot (350) further approximates anvil half (314) and cartridge half (312) while resilient interlock (302) is spread apart such that spring arms (304, 306) no longer block the rotation of clamp lever (340). Stated differently, anvil ramps (361) fully engage spring arms (304 306) and expand upper portions (308) laterally outwardly, away from one another, providing both upper portions (308) in a fully expanded state and withdrawn from latch pin slots (323). In the fully expanded state of spring arms (304, 306), clamp lever (340) is permitted to rotate from the open position to the closed position so that linear surgical stapler (310) may be clamped on tissue.

Figure 22D:
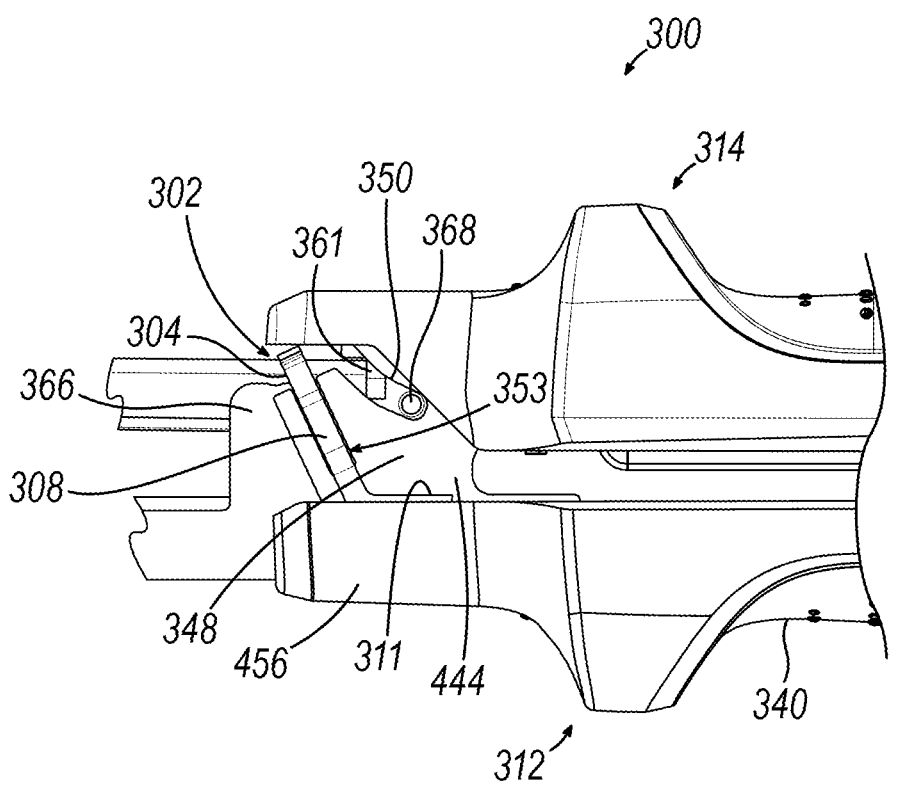
FIG. 22D depicts an enlarged side elevational view of the linear surgical stapler of FIG. 19, showing the interlock spring fully spread by the ramp of the anvil half with the clamp lever in the closed position.

FIG. 22D shows the linear surgical stapler (310) in the closed position after the anvil half (314) is fully approximated relative to cartridge half (312). Anvil ramps (361) in the closed position are positioned within latch pin slots (323) along with latch pin (368), and resilient interlock (302) remains in the fully expanded state. Upper portions (308) in the expanded state are driven across an outer surface of cartridge channel flanges (366) until clamp lever (340) comes to rest in the closed position. Once the clamp lever (340) is in the closed position, the firing assembly (410) may be actuated to properly cut and staple tissue.

III. ILLUSTRATIVE COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a housing configured to be fixedly coupled to a frame of a linear surgical stapler, wherein the linear surgical stapler includes a first stapler half having the frame and a clamp lever pivotably coupled with the frame, and a second stapler half having a latch projection configured to be captured by the clamp lever when the clamp lever is actuated to a closed state to approximate the first and second stapler halves to clamp tissue therebetween; (b) a lockout arm rotatably coupled to the housing, wherein the lockout arm is rotatable relative to the housing between a lockout position and a bypass position, wherein the lockout arm in the lockout position is configured to inhibit a proximal end of the clamp lever in the closed state from coupling with a proximal end of the frame, wherein the lockout arm in the bypass position is configured to permit the proximal end of the clamp lever in the closed state to couple with the proximal end of the frame; and (c) a spring configured to resiliently bias the lockout arm toward the lockout position, wherein the lockout arm is configured to transition from the lockout position to the bypass position only when the latch projection is properly captured by the clamp lever in the closed state.

Example 2

The apparatus of Example 1, wherein the first stapler half has a distal end configured to receive a staple cartridge.

Example 3

The apparatus of any of the preceding Examples, wherein the housing is configured to be secured to a frame sidewall of the frame.

Example 4

The apparatus of Example 3, wherein the housing includes one or more engagement features configured to engage the frame sidewall to retain the housing in a fixed position relative to the frame.

Example 5

The apparatus of Example 4, wherein each engagement feature includes an angled portion and a recessed portion, wherein the angled portion is configured to resiliently deflect and pass through an aperture of the frame sidewall so that the recessed portion resides within the aperture, wherein the angled portion is configured to inhibit removal of the housing from the frame.

Example 6

The apparatus of any of Examples 4 through 5, wherein the housing includes a recessed portion and at least one raised portion, wherein the recessed portion is configured to receive a portion of the lockout arm and permit rotation of the lockout arm relative to the housing between the lockout position and the bypass position.

Example 7

The apparatus of Example 6, wherein the at least one raised portion comprises a pair of raised portions, wherein the raised portions are configured to be positioned against the frame sidewall to inhibit lateral movement of the lockout arm relative to the frame when the engagement features are engaged with the frame sidewall.

Example 8

The apparatus of any of the preceding Examples, wherein the lockout arm includes a proximal arm end, a distal arm end, and a pivot positioned between the proximal and distal arm ends, wherein in the lockout position the proximal arm end is configured to engage a latch member at the proximal end of the first stapler half and thereby inhibit the proximal end of the clamp lever from coupling with the proximal end of the frame when the latch projection is not properly captured by the clamp lever in the closed state.

Example 9

The apparatus of any Example 8, wherein in the bypass position the lockout arm is configured to extend parallel with a longitudinal axis of the linear surgical stapler, wherein in the lockout position the lockout arm is configured to extend obliquely relative to the longitudinal axis.

Example 10

The apparatus of any of Examples 8 through 9, wherein the distal arm end is configured to engage and be actuated by the second stapler half to rotate the lockout arm from the lockout position to the bypass position against the bias of the spring when the latch projection is properly captured by the clamp lever in the closed state.

Example 11

The apparatus of Example 10, wherein the distal arm end includes a distal tab configured to engage a shroud of the second stapler half to rotate the lockout arm from the lockout position to the bypass position when the latch projection is properly captured by the clamp lever in the closed state.

Example 12

The apparatus of any of Examples 10 through 11, wherein the proximal arm end includes a proximal tab configured to engage a latch member at a proximal end of the first stapler half and thereby inhibit the latch member from coupling the proximal end of the clamp lever with the proximal end of the frame when the latch projection is not properly captured by the clamp lever in the closed state.

Example 13

The apparatus of any of the preceding Examples, wherein the spring comprises a compression spring.

Example 14

A surgical instrument assembly comprising: (a) the apparatus of claim 1; and (b) a linear surgical stapler.

Example 15

The surgical instrument assembly of Example 14, wherein the linear surgical stapler includes: (i) a first stapler half configured to receive a staple cartridge with a plurality of staples, and (ii) a second stapler half having an anvil with a plurality of staple forming pockets, wherein one of the first stapler half or the second stapler half includes a latch projection, wherein the other of the first stapler half or the second stapler half includes a clamp member movable from a first position to a second position to capture the latch projection and thereby approximate the first and second stapler halves to clamp tissue therebetween, wherein the apparatus is mounted to the other of the first stapler half or the second stapler half.

Example 16

An apparatus comprising: (a) a linear surgical stapler comprising: (i) a first staple half having a distal portion configured to present a first stapling surface, (ii) a second stapler half having a distal portion configured to present a second stapling surface, wherein the first and second elongate members are configured to releasably couple together to enable the first and second stapling surfaces to cooperate to clamp and staple tissue with a plurality of staples, (iii) a clamp member presented by one of the first stapler half or the second stapler half, wherein the clamp member is movable from a first position to a second position to approximate the first and second stapling surfaces for clamping tissue, and (iv) a latch member configured to transition from an unlatched state to a latched state to releasably retain the clamp member in the second position; and (b) an interlock device configured to inhibit at least one of the following when the first and second stapler halves are not properly aligned with one another: (i) transitioning of the clamp lever from the first position to the second position, or (ii) transitioning of the latch member from the unlatched state to the latched state.

Example 17

The apparatus of Example 16, wherein the interlock device is mounted to one of the first stapler half or the second stapler half and includes a moveable lockout arm, wherein the movable lockout arm is actuatable by the other of the first stapler half or the second stapler half from a lockout position to a bypass position when the first and second stapler halves are properly aligned with one another.

Example 18

The apparatus of Example 17, wherein the clamp member is presented by the first stapler half, wherein the lockout arm is configured to releasably engage a portion of the first stapler half in the lockout position.

Example 19

A method of operating a linear surgical stapler that includes a first stapler half having a stapling assembly with a plurality of staples, a second stapler half having an anvil with a plurality of staple forming pockets, a clamp lever presented by one of the first stapler half or the second stapler half, and a latch projection presented by the other of the first stapler half or the second stapler half, the method comprising: (a) mating a proximal end of the first stapler half with a proximal end of the second stapler half; (b) approximating distal ends of the first and second stapler halves while the clamp lever is in an open position so that the clamp lever is positioned to receive the latch projection; (c) actuating a lockout arm of the one of the first stapler half or the second stapler half with the other of the first stapler half or the second stapler half so that the lockout arm moves from a lockout position to a bypass position, wherein the lockout arm in the lockout position is configured to inhibit the clamp lever from at least one of rotating from the open position to closed position or latching with a proximal end of the one of the first stapler half or the second stapler half; and (d) with the lockout arm in the bypass position, rotating the clamp lever toward the closed position in which the latch projection is captured by the clamp lever to further approximate the distal ends of the first and second stapler halves and in which the proximal end of the clamp lever latches with the proximal end of the one of the first stapler half or the second stapler half.

Example 20

The apparatus of Example 19, wherein the clamp lever and the lockout arm are presented by the first stapler half, wherein the latch projection is presented by the second stapler half, wherein actuating the lockout arm from the lockout position to the bypass position comprises actuating the lockout arm with the second stapler half.

IV. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more teachings disclosed herein may be combined with any one or more teachings disclosed in U.S. Pat. No. 10,631,866, entitled "Release Mechanism for Linear Surgical Stapler," issued Apr. 28, 2020; U.S. Pat. No. 10,667,818, entitled "Lockout Assembly for Linear Surgical Stapler," issued Jun. 2, 2020; U.S. Pat. No. 10,932,781, entitled "Features to Align and Close Linear Surgical Stapler," issued Mar. 2, 2021; U.S. Pat. No. 10,898,197, entitled "Releasable Coupling Features for Proximal Portions of Linear Surgical Stapler," issued Jan. 26, 2021; U.S. Pat. No. 10,874,398, entitled "Firing Lever Assembly for Linear Surgical Stapler," issued Dec. 29, 2020; U.S. Pat. No. 10,687,819, entitled "Clamping Mechanism for Linear Surgical Stapler," issued Jun. 23, 2020; U.S. Pat. No. 10,898,187, entitled "Firing System for Linear Surgical Stapler," issued Jan. 26, 2021; U.S. Pat. No. 11,033,266, entitled "Decoupling Mechanism for Linear Surgical Stapler, issued Jun. 15, 2021; U.S. Pat. No. 11,045,193, entitled "Anvil Assembly for Linear Surgical Stapler," issued Jun. 29, 2021; U.S. Pat. No. 10,905,419, entitled "Closure Assembly for Linear Surgical Stapler," issued Feb. 2, 2021; U.S. Pat. No. 11,278,285, entitled "Clamping Assembly for Linear Surgical Stapler," issued Mar. 22, 2022; U.S. Pat. No. 11,229,433, entitled "Linear Surgical Stapler," issued Jan. 25, 2022; U.S. Pub. No. 2022/0142641, entitled "System and Method for Forming Pockets in Anvil of Surgical Stapler," published May 12, 2022, issued as U.S. Pat. No. 12,016,555 on Jun. 25, 2024; U.S. Pat. No. 11,224,425, entitled "Surgical Linear Cutter Wishbone Separation Mechanism with Detent," issued Jan. 18, 2022; U.S. Pat. No. 11,219,454, entitled "Pin Trap Mechanism for Surgical Linear Cutter," issued Jan. 11, 2022; U.S. Pub. No. 2021/0369272, entitled "Separation Mechanism for Surgical Linear Cutter," published Dec. 2, 2021, issued as U.S. Pat. No. 11,399,827 on Aug. 2, 2022; U.S. patent application Ser. No. 17/489,879, entitled "Lockout Feature for Linear Surgical Stapler Cartridge," filed Sep. 30, 2021, issued as U.S. Pat. No. 11,937,812 on Mar. 26, 2024; U.S. patent application Ser. No. 29/842,580, entitled "Staple Cartridge for Linear Surgical Stapler," filed Jun. 16, 2022, issued as U.S. Des. Pat. No. D1,076,431 on Mar. 18, 2025; and/or U.S. patent application Ser. No. 29/842,581, entitled "Linear Surgical Stapler," filed Jun. 16, 2022. The disclosure of each of these references is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as any of the systems made available by Auris Health, Inc. of Redwood City, California or by Intuitive Surgical, Inc. of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
(a) a housing configured to be fixedly coupled to a frame of a linear surgical stapler, wherein the linear surgical stapler includes a first stapler half having the frame and a clamp lever pivotably coupled with the frame, and a second stapler half having a latch projection configured to be captured by the clamp lever when the clamp lever is actuated to a closed state to approximate the first and second stapler halves to clamp tissue therebetween;
(b) a lockout arm rotatably coupled to the housing, wherein the lockout arm is rotatable relative to the housing between a lockout position and a bypass position, wherein the lockout arm in the lockout position is configured to inhibit a proximal end of the clamp lever in the closed state from coupling with a proximal end of the frame, wherein the lockout arm in the bypass position is configured to permit the proximal end of the clamp lever in the closed state to couple with the proximal end of the frame; and
(c) a spring configured to resiliently bias the lockout arm toward the lockout position,
wherein the lockout arm is configured to transition from the lockout position to the bypass position only when the latch projection is properly captured by the clamp lever in the closed state.

2. The apparatus of claim 1, wherein the first stapler half has a distal end configured to receive a staple cartridge.

3. The apparatus of claim 1, wherein the housing is configured to be secured to a frame sidewall of the frame.

4. The apparatus of claim 3, wherein the housing includes one or more engagement bodies configured to engage the frame sidewall to retain the housing in a fixed position relative to the frame.

5. The apparatus of claim 4, wherein each engagement body includes an angled portion and a recessed portion, wherein the angled portion is configured to resiliently deflect and pass through an aperture of the frame sidewall so that the recessed portion resides within the aperture, wherein the angled portion is configured to inhibit removal of the housing from the frame.

6. The apparatus of claim 4, wherein the housing includes a recessed portion and at least one raised portion, wherein the recessed portion is configured to receive a portion of the lockout arm and permit rotation of the lockout arm relative to the housing between the lockout position and the bypass position.

7. The apparatus of claim 6, wherein the at least one raised portion comprises a pair of raised portions, wherein the raised portions are configured to be positioned against the frame sidewall to inhibit lateral movement of the lockout arm relative to the frame when the engagement features are engaged with the frame sidewall.

8. The apparatus of claim 1, wherein the lockout arm includes a proximal arm end, a distal arm end, and a pivot positioned between the proximal and distal arm ends, wherein in the lockout position the proximal arm end is configured to engage a latch at the proximal end of the first stapler half and thereby inhibit the proximal end of the clamp lever from coupling with the proximal end of the frame when the latch projection is not properly captured by the clamp lever in the closed state.

9. The apparatus of claim 8, wherein in the bypass position the lockout arm is configured to extend parallel with a longitudinal axis of the linear surgical stapler, wherein in the lockout position the lockout arm is configured to extend obliquely relative to the longitudinal axis.

10. The apparatus of claim 8, wherein the distal arm end is configured to engage and be actuated by the second stapler half to rotate the lockout arm from the lockout position to the bypass position against the bias of the spring when the latch projection is properly captured by the clamp lever in the closed state.

11. The apparatus of claim 10, wherein the distal arm end includes a distal tab configured to engage a shroud of the second stapler half to rotate the lockout arm from the lockout position to the bypass position when the latch projection is properly captured by the clamp lever in the closed state.

12. The apparatus of claim 10, wherein the proximal arm end includes a proximal tab configured to engage a latch at a proximal end of the first stapler half and thereby inhibit the latch from coupling the proximal end of the clamp lever with the proximal end of the frame when the latch projection is not properly captured by the clamp lever in the closed state.

13. The apparatus of claim 1, wherein the spring comprises a compression spring.

14. A surgical instrument assembly comprising:

(a) the apparatus of claim 1; and (b) a linear surgical stapler.

15. The surgical instrument assembly of claim 14, wherein the linear surgical stapler includes:

(i) a first stapler half configured to receive a staple cartridge with a plurality of staples, and (ii) a second stapler half having an anvil with a plurality of staple forming pockets, wherein one of the first stapler half or the second stapler half includes a latch projection, wherein the other of the first stapler half or the second stapler half includes a clamp lever movable from a first position to a second position to capture the latch projection and thereby approximate the first and second stapler halves to clamp tissue therebetween, wherein the apparatus is mounted to the other of the first stapler half or the second stapler half.

16. An apparatus comprising:

(a) a linear surgical stapler comprising:

(i) a first staple half having a distal portion configured to present a first stapling surface, (ii) a second stapler half having a distal portion configured to present a second stapling surface, wherein the first and second stapler halves are configured to releasably couple together to enable the first and second stapling surfaces to cooperate to clamp and staple tissue with a plurality of staples, (iii) a clamp presented by one of the first stapler half or the second stapler half, wherein the clamp is movable from a first position to a second position to approximate the first and second stapling surfaces for clamping tissue, and (iv) a latch configured to transition from an unlatched state to a latched state to releasably retain the clamp in the second position; and (b) an interlock device having a resilient portion and thereby being configured to inhibit at least one of the following when the first and second stapler halves are not properly aligned with one another:

(i) transitioning of the clamp from the first position to the second position, or (ii) transitioning of the latch from the unlatched state to the latched state.

17. The apparatus of claim 16, wherein the interlock device is mounted to one of the first stapler half or the second stapler half and includes a movable lockout arm, wherein the movable lockout arm is actuatable by the other of the first stapler half or the second stapler half from a lockout position to a bypass position when the first and second stapler halves are properly aligned with one another.

18. The apparatus of claim 17, wherein the clamp is presented by the first stapler half, wherein the lockout arm is configured to releasably engage a portion of the first stapler half in the lockout position.

19. A method of operating a linear surgical stapler that includes a first stapler half having a stapling assembly with a plurality of staples, a second stapler half having an anvil with a plurality of staple forming pockets, a clamp lever presented by one of the first stapler half or the second stapler half, and a latch projection presented by the other of the first stapler half or the second stapler half, the method comprising:

(a) mating a proximal end of the first stapler half with a proximal end of the second stapler half;

(b) approximating distal ends of the first and second stapler halves while the clamp lever is in an open position so that the clamp lever is positioned to receive the latch projection;

(c) actuating a lockout arm of the one of the first stapler half or the second stapler half with the other of the first stapler half or the second stapler half so that the lockout arm overcomes a resilient bias and moves from a lockout position to a bypass position, wherein the lockout arm in the lockout position is configured to inhibit the clamp lever from at least one of rotating from the open position to closed position or latching with a proximal end of the one of the first stapler half or the second stapler half; and (d) with the lockout arm in the bypass position, rotating the clamp lever toward the closed position in which the latch projection is captured by the clamp lever to further approximate the distal ends of the first and second stapler halves and in which the proximal end of the clamp lever latches with the proximal end of the one of the first stapler half or the second stapler half.

20. The method of claim 19, wherein the clamp lever and the lockout arm are presented by the first stapler half, wherein the latch projection is presented by the second stapler half, wherein actuating the lockout arm from the lockout position to the bypass position comprises actuating the lockout arm with the second stapler half.

* * * * *